(12) United States Patent
Wolkowicz

(10) Patent No.: US 10,676,729 B2
(45) Date of Patent: *Jun. 9, 2020

(54) COMPOSITIONS AND METHODS FOR IDENTIFYING PROTEASE INHIBITORS

(71) Applicant: San Diego State University (SDSU) Foundation, San Diego, CA (US)

(72) Inventor: Roland Wolkowicz, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 255 days.

This patent is subject to a terminal disclaimer.

(21) Appl. No.: 15/399,339

(22) Filed: Jan. 5, 2017

(65) Prior Publication Data

US 2017/0191988 A1    Jul. 6, 2017

Related U.S. Application Data

(60) Provisional application No. 62/275,556, filed on Jan. 6, 2016.

(51) Int. Cl.
*C12N 9/64* (2006.01)
*C12Q 1/37* (2006.01)
*C12N 15/62* (2006.01)
*C12N 15/52* (2006.01)

(52) U.S. Cl.
CPC ........... *C12N 9/6421* (2013.01); *C12N 15/52* (2013.01); *C12N 15/625* (2013.01); *C12Q 1/37* (2013.01)

(58) Field of Classification Search
None
See application file for complete search history.

(56) References Cited

U.S. PATENT DOCUMENTS

| 9,169,312 | B2 * | 10/2015 | Wolkowicz | ...... C07K 14/70517 |
| 9,518,254 | B2 * | 12/2016 | Wolkowicz | ............ C12N 9/506 |
| 9,683,254 | B2 * | 6/2017 | Wolkowicz | ...... C07K 14/70517 |
| 10,006,077 | B2 * | 6/2018 | Wolkowicz | ...... C07K 14/70517 |
| 2019/0048391 | A1 * | 2/2019 | Wolkowicz | .............. C12Q 1/37 |

* cited by examiner

*Primary Examiner* — Anand U Desai
(74) *Attorney, Agent, or Firm* — Greer, Burns & Crain, LTD.; Gregory P. Einhorn

(57) ABSTRACT

Provided are compositions, e.g., multiplexed platforms or systems, to screen for molecules, e.g., small molecule active agents such as drugs, that inhibit enzymes such as proteases. Provided are cell-based or multiplexed platforms for monitoring or assay the activity of a protease. Provided are cell-based assays and multiplexed systems for the monitoring of enzyme, activity such as proteolytic cleavage on the cell surface, where optionally the protein, e.g., an enzyme, can be naturally expressed on the cell surface or engineered to be expressed on the cell's surface. Provided are cells and stable cell lines expressing an "assay construct" and an enzyme of interest, where optionally one cell or cell line expresses both the "assay construct" and the enzyme, or two different cells or independent cell lines are used and mixed in the assay, where one expresses the "assay construct" with the enzyme substrate and the second expressing the enzyme.

21 Claims, 26 Drawing Sheets
(26 of 26 Drawing Sheet(s) Filed in Color)
Specification includes a Sequence Listing.

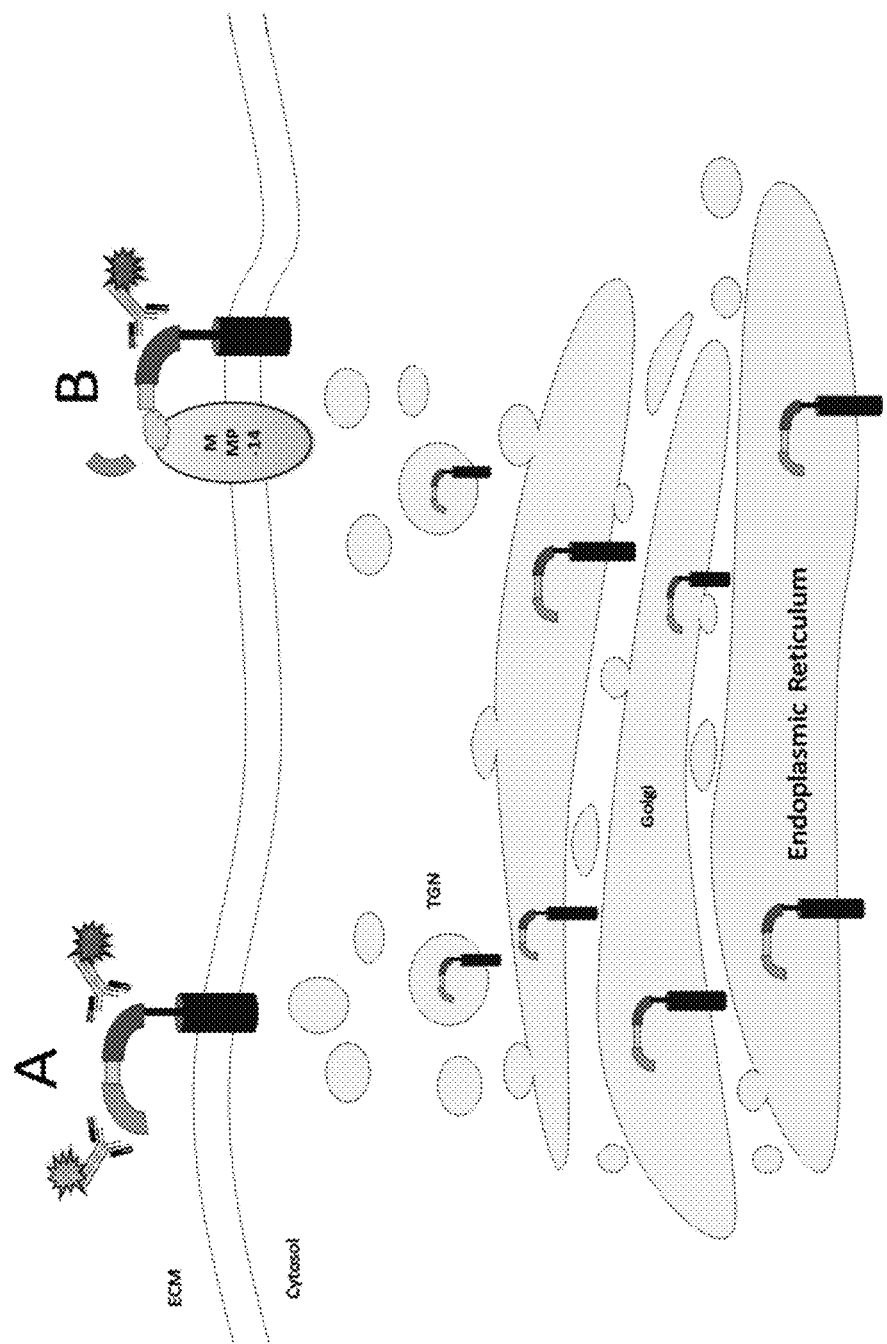

SEQUENCE LISTING

```
<160> NUMBER OF SEQ ID NOS: 16

<210> SEQ ID NO 1
<211> LENGTH: 10
<212> TYPE: PRT
<213> ORGANISM: artificial sequence
<220> FEATURE:
<223> OTHER INFORMATION: synthetic peptide

<400> SEQUENCE: 1

Cys Arg Pro Ala His Leu Arg Asp Ser Gly
1               5                   10

<210> SEQ ID NO 2
<211> LENGTH: 6
<212> TYPE: PRT
<213> ORGANISM: artificial sequence
<220> FEATURE:
<223> OTHER INFORMATION: synthetic peptide

<400> SEQUENCE: 2

Gly Gly Ser Gly Gly Thr
1               5

<210> SEQ ID NO 3
<211> LENGTH: 4
<212> TYPE: PRT
<213> ORGANISM: artificial sequence
<220> FEATURE:
<223> OTHER INFORMATION: synthetic peptide

<400> SEQUENCE: 3

Ala His Leu Arg
1

<210> SEQ ID NO 4
<211> LENGTH: 5
<212> TYPE: PRT
<213> ORGANISM: artificial sequence
<220> FEATURE:
<223> OTHER INFORMATION: synthetic peptide

<400> SEQUENCE: 4

Gly Gly Gly Gly Ser
1               5
```

```
<210> SEQ ID NO 5
<211> LENGTH: 40
<212> TYPE: DNA
<213> ORGANISM: artificial sequence
<220> FEATURE:
<223> OTHER INFORMATION: synthetic oligonucleotide

<400> SEQUENCE: 5
tataagatct ggcggctccg gcgtgagcaa gggcgaggag                40

<210> SEQ ID NO 6
<211> LENGTH: 37
<212> TYPE: DNA
<213> ORGANISM: artificial sequence
<220> FEATURE:
<223> OTHER INFORMATION: synthetic oligonucleotide

<400> SEQUENCE: 6
tataggatcc accggtttta tagagctcgt ccatgcc                  37

<210> SEQ ID NO 7
<211> LENGTH: 38
<212> TYPE: DNA
<213> ORGANISM: artificial sequence
<220> FEATURE:
<223> OTHER INFORMATION: synthetic oligonucleotide

<400> SEQUENCE: 7
tatatagaat tcccaccatg tctcccgccc caagaccc                 38

<210> SEQ ID NO 8
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 8
tatatagcta gctcagacct tgtccagcag ggaacg                   36

<210> SEQ ID NO 9
<211> LENGTH: 10
<212> TYPE: PRT
<213> ORGANISM: artificial sequence
<220> FEATURE:
<223> OTHER INFORMATION: synthetic peptide

<400> SEQUENCE: 9

Cys Arg Pro Ala Ala Leu Ala Asp Ser Gly
1               5                   10

<210> SEQ ID NO 10
<211> LENGTH: 13
<212> TYPE: PRT
<213> ORGANISM: artificial sequence
<220> FEATURE:
<223> OTHER INFORMATION: synthetic peptide

<400> SEQUENCE: 10

Cys Pro Lys Glu Ser Cys Asn Leu Phe Val Leu Lys Asp
1               5                   10

<210> SEQ ID NO 11
<211> LENGTH: 13
<212> TYPE: PRT
<213> ORGANISM: artificial sequence
<220> FEATURE:
```

```
<223> OTHER INFORMATION: synthetic peptide

<400> SEQUENCE: 11

Cys Pro Lys Glu Ser Cys Ile Val Phe Val Leu Lys Asp
1               5                   10

<210> SEQ ID NO 12
<211> LENGTH: 8
<212> TYPE: PRT
<213> ORGANISM: artificial sequence
<220> FEATURE:
<223> OTHER INFORMATION: synthetic peptide

<400> SEQUENCE: 12

Asp Tyr Lys Asp Asp Asp Asp Lys
1               5

<210> SEQ ID NO 13
<211> LENGTH: 9
<212> TYPE: PRT
<213> ORGANISM: artificial sequence
<220> FEATURE:
<223> OTHER INFORMATION: synthetic peptide

<400> SEQUENCE: 13

Tyr Pro Tyr Asp Val Pro Asp Tyr Ala
1               5

<210> SEQ ID NO 14
<211> LENGTH: 4
<212> TYPE: PRT
<213> ORGANISM: artificial sequence
<220> FEATURE:
<223> OTHER INFORMATION: synthetic peptide

<400> SEQUENCE: 14

Ala Ala Leu Ala
1

<210> SEQ ID NO 15
<211> LENGTH: 4
<212> TYPE: PRT
<213> ORGANISM: artificial sequence
<220> FEATURE:
<223> OTHER INFORMATION: synthetic peptide

<400> SEQUENCE: 15

Cys Asn Leu Phe
1

<210> SEQ ID NO 16
<211> LENGTH: 4
<212> TYPE: PRT
<213> ORGANISM: artificial sequence
<220> FEATURE:
<223> OTHER INFORMATION: synthetic peptide

<400> SEQUENCE: 16

Cys Ile Val Phe
1
```

COMPOSITIONS AND METHODS FOR IDENTIFYING PROTEASE INHIBITORS

RELATED APPLICATIONS

This U.S. utility patent Application claims the benefit of priority under 35 U.S.C. § 119(e) of U.S. Provisional Application No. 62/275,556, filed Jan. 6, 2016. The aforementioned application is expressly incorporated herein by reference in its entirety and for all purposes.

TECHNICAL FIELD

This invention relates to molecular and cellular biology, biochemistry, molecular genetics, and drug design and discovery. In alternative embodiments, provided are compositions, e.g., multiplexed platforms or systems, to screen for molecules, e.g., small molecule active agents such as drugs, that inhibit protein activity, e.g., enzymes such as proteases. In one embodiment, provided are a cell-based or multiplexed platform or system for monitoring or assaying the activity of a protein, e.g., an enzyme, e.g., a protease. In alternative embodiments, provided are cell-based assays and multiplexed platforms or systems for the monitoring or assaying of protein, e.g., an enzyme, activity such as proteolytic cleavage on the cell surface, where optionally the protein, e.g., an enzyme, can be naturally expressed on the cell surface or engineered to be expressed on the cell's surface. In alternative embodiments, provided are cells and stable cell lines expressing an "assay construct" as provided herein (containing a cleavable enzyme substrate) and the protein, e.g., an enzyme, of interest, where optionally one cell or cell line expresses both the "assay construct" and the protein, e.g., an enzyme, or alternatively two different cells or independent cell lines are used and mixed in the assay, where one expresses the "assay construct" with the protein or enzyme substrate and the second expressing the protein or enzyme.

BACKGROUND

Proteolysis is a cleavage event of a protein that commonly occurs to serve several biological purposes such as zymogen activation, protein degradation, and immune response[1-3]. Most proteolytic cleavage event occur in the classical secretory pathway, which involves the passage of proteins targeted for post-translational modifications through the Endoplasmic Reticulum (ER) and trans-Golgi network. The main proteases required for proteolysis in the intracellular compartment include enzymes from signal peptidases (SP), signal peptide peptidases (SPP), and pro-protein convertase (PC) families[4-6].

Many proteins are synthesized with signal sequence or signal targeting for secretion or site-specific transport. Most signal sequences are about 20-30 amino acids in the N-terminus of a protein, and they are often cleaved by SP or SPP upon the transverse of newly translated proteins in the lumen of the ER. Moreover, proteins can be further cleaved by PC such as Furin or PC1 in order to render the protein functional or active. The classic example of such cleavage processing by SP, SPP, and PC is the cleavage of pre-pro-insulin by SP or/and SPP into its inactive pro-insulin, which will further be cleaved by PC into active insulin before being transported across the cell membrane as illustrated in FIG. 1.

Despite the fewer events that are present in cells, proteolysis events are also known to occur in the extracellular portion of the cells, granted that the event might produce different purposes than its intracellular counterpart. Some examples of extracellular proteolysis include the cleavage of E-Cadherin by ADAM-10 protease and the cleavage of Sialic Acid receptor protein by Neuraminidase (NA) in Influenza Virus budding[36]. Another prominent group of proteases that cleaves substrates in the extracellular membrane is Matrix Metalloproteases (MMPs).

MMPs have been of tremendous clinical significance due to recent evidence of their roles in the progression of cancer, atherosclerosis, aneurism, and arthritis[7,8]. MMP-14 is a ubiquitously-expressed cell surface protease known to activate several soluble MMPs (s-MMPs) via extracellular proteolysis. Active s-MMPs are then used for the restructuring of the extracellular matrix (ECM) that could facilitate cell migration and development. MMP-14 is known to be highly expressed in cancer tissues, as cells require constant remodeling of the ECM to accommodate fast replication and migration that leads to metastasis.

SUMMARY

In alternative embodiments, provided are cell-based methods, cell-based platforms or systems, or multiplexed platforms or systems, for monitoring or assaying the activity of an enzyme or protease on an extracellular surface (or outer membrane, e.g., of a liposome, an exosome) and/or in the extracellular matrix (ECM).

In alternative embodiments, provided are: a cell-based method, a cell-based platform or system or a multiplexed platform or system (e.g., a high through-put platform), for monitoring or assaying the activity of an enzyme, e.g., a protease, comprising (or made by a method comprising):

(1) (a) providing a nucleic acid encoding a scaffold protein operatively linked to a transcriptional regulatory unit, wherein the scaffold protein comprises:
  (i) a signal sequence (SS) or any amino acid motif that places the scaffold protein on the extracellular surface of the cell, or on the outer surface of a membrane, a liposome or an exosome;
  (ii) a first tag capable of being specifically recognized by or bound to by a first detectable moiety, optionally a first epitope tag capable of being specifically recognized by or bound to by a first antibody or epitope binding unit, wherein the antibody is detectable, wherein optionally the antibody or epitope binding unit is a fluorescently tagged;
  (iii) an amino acid motif or subsequence susceptible to cleavage by the enzyme, or protease, under physiologic or cell culture conditions;
  (iv) a second tag capable of being specifically recognized by or bound to by a second detectable moiety, optionally a second epitope tag capable of being specifically recognized by or bound to by a second antibody or epitope binding unit, wherein the antibody is detectable, wherein optionally the antibody or epitope binding unit is a fluorescently tagged antibody; and
  (v) a transmembrane domain or moiety attaching the scaffold protein to the extracellular surface, or on the outer surface of a membrane, a liposome or an exosome, or keeping the scaffold protein onto the extracellular surface, or on the outer surface of the membrane, liposome or exosome,
  wherein the first detectable moiety (e.g., antibody or epitope binding unit) that binds to or recognizes the first epitope tag does not bind to or recognize the second epitope tag, and the second detectable moiety (e.g., antibody or epitope binding unit) that binds or recognizes the second epitope tag does not bind to or recognize the first epitope tag;

wherein optionally the nucleic acid encoding the scaffold protein further comprises a sequence encoding a flexible peptide linker, optionally the flexible peptide linker comprises a glycine-comprising linker, optionally a four-, 5- or 6-glycine linker, optionally 1 to six repeats of a glycine linker GGGGS, optionally the flexible linker is positioned between the transmembrane domain or moiety attaching the scaffold protein to the extracellular surface, or the outer surface of the membrane, liposome or exosome, or keeping the scaffold protein onto the extracellular surface, or the outer surface of the membrane, liposome or exosome, and the membrane-proximal tag;

and optionally one of the tags comprises a FLAG tag (DYKDDDDK) SEQ ID NO:12) or an HA tag (YPYDVPDYA) (SEQ ID NO:13), and optionally further comprising a fluorescent protein positioned in the scaffold protein amino terminal to the tag distal to the cell surface, optionally the fluorescent protein comprises an mCitrine fluorescence protein;

(b) providing a nucleic acid encoding the enzyme or protease in a construct that places the enzyme or protease on the cell surface or expresses the enzyme or protease extracellularly, or providing the enzyme or protease to the extracellular surface of the cell, or to the outer surface of a membrane, a liposome or an exosome, wherein optionally the protease or enzyme assayed is endogenous to the cell and is expressed on the cell surface;

(c) inserting or transfecting the nucleic acid of (a), and (b) if the enzyme or protease is provided by expressing a nucleic acid, into the cell if the cell does not already express a heterologous or endogenous enzyme or protease; and (d) co-expressing the nucleic acid of (a) and (b) in the cell, or expressing the nucleic acid of (a) in the cell if the cell already expresses a heterologous or endogenous enzyme or protease, wherein optionally the protease comprises a viral protease or HIV-1 protease, or a Hepacivirus such as a Hepatitis C Virus (HCV) or a Flaviviridae virus such as a Zika virus or a Dengue Virus (DenV) protease, G47, a Filoviridae virus such as an Ebolavirus, optionally determining whether the scaffold protein is expressed and attached or otherwise held onto the extracellular surface of the cell, or the outer surface of the membrane, liposome or exosome;

(2) the cell-based method, cell-based platform or system or multiplexed platform or system of (1), further comprising screening for an inhibitor or competitor of the enzyme or protease by:

(a) providing a compound to be screened as an inhibitor or competitor of the enzyme or protease;

(b) contacting a plurality of the cells expressing the scaffold protein on their extracellular surfaces, or on the outer surface of a membrane, a liposome or an exosome, or extracellular matrices (ECM) with the compound, optionally culturing the cells for a period of time (optionally one minute to one hour); and (c) determining whether the second or membrane-distal tag of the scaffold protein remains expressed on the extracellular surface, or on the outer surface of a membrane, a liposome or an exosome, or ECM of the cell, wherein detecting the presence of the second or membrane-distal tag of the scaffold protein on the cell or in the ECM indicates that the enzyme or protease is significantly inhibited by the compound, and not detecting the presence of the second or membrane-distal tag of the scaffold protein on the cell or in the ECM indicates that the enzyme or protease is not significantly inhibited by the compound;

(3) the cell-based method, cell-based platform or system or multiplexed platform or system of any of (1) to (2), further comprising running a negative control comprising dividing the plurality of the cells co-expressing the scaffold-expressing nucleic acid and not adding the compound to be screened as an inhibitor to one of the divided cell samples;

(4) the cell-based method, cell-based platform or system or multiplexed platform or system of any of (1) to (3), further comprising running a positive control comprising dividing the plurality of the cells co-expressing the scaffold-expressing nucleic acid and adding a known inhibitor or competitor of the enzyme or protease to one of the divided cell samples;

(5) the cell-based method, cell-based platform or system or multiplexed platform or system of any of (1) to (4), wherein the scaffold-expressing nucleic acid comprises a transcriptional regulatory unit comprising a promoter, optionally an inducible promoter or a constitutive promoter;

(6) the cell-based method, cell-based platform or system or multiplexed platform or system of any of (1) to (5), wherein the cell is a mammalian cell, a monkey cell or a human cell, or a lymphocyte or a hepatocyte, or a T cell, and optionally the cells are genetically bar-coded;

(7) the cell-based method, cell-based platform or system or multiplexed platform or system of any of (1) to (6), wherein a detectable moiety is detected or measured on the extracellular surface of the cell, or on the outer surface of a membrane, a liposome or an exosome, by a high throughput screen, a plate-reader, a flow cytometry or microscope visualization;

(8) the cell-based method, cell-based platform or system or multiplexed platform or system of any of (1) to (7), wherein the compound to be screened as an inhibitor or competitor of the enzyme or protease comprises a small molecule, a nucleic acid, a polypeptide or peptide, a peptidomimetic, a polysaccharide or a lipid, or is a member of a library of compounds to be screened, or is a member of a random peptide library or a chemical compound library; or (9) the cell-based method, cell-based platform or system or multiplexed platform or system of any of (1) to (8), wherein two or more, or a plurality of enzymes or proteases are screened in the same cell, or on separate cells (and optionally the cells are mixed in the assay), wherein optionally they are variants of the same enzyme or protease, or different enzymes or proteases, or a combination thereof.

In alternative embodiments, provided are isolated, recombinant or synthetic or chimeric nucleic acids encoding a scaffold protein as provided herein, optionally operatively linked to a transcriptional regulatory unit, wherein optionally the transcriptional regulatory unit comprising a promoter, optionally an inducible promoter or a constitutive promoter.

In alternative embodiments, provided are: a vector, expression cassette, cosmid or plasmid comprising (or having contained therein) an isolated, recombinant or synthetic or chimeric nucleic acid as provided herein.

In alternative embodiments, provided are: isolated, recombinant or synthetic or chimeric polypeptides, e.g., chimeric or "scaffold" polypeptides, encoded by the nucleic acid as provided herein.

In alternative embodiments, provided are: chimeric polypeptides or scaffold proteins, comprising or consisting of:

(a) a signal sequence (SS) or any amino acid motif that places the chimeric polypeptide or scaffold protein on the extracellular surface of the cell, or on the outer surface of a membrane, a liposome or an exosome;

(b) a first tag capable of being specifically recognized by or bound to by a first detectable moiety, optionally a first epitope tag capable of being specifically recognized by or bound to by a first antibody or epitope binding unit, wherein the antibody is detectable, wherein optionally the antibody or epitope binding unit is a fluorescently tagged;

(c) an amino acid motif or subsequence susceptible to cleavage by the enzyme or protease under physiologic or cell culture conditions;

(d) a second tag capable of being specifically recognized by or bound to by a second detectable moiety, optionally a second epitope tag capable of being specifically recognized by or bound to by a second antibody or epitope binding unit, wherein the antibody is detectable, wherein optionally the antibody or epitope binding unit is a fluorescently tagged antibody; and (e) a transmembrane domain or moiety attaching the chimeric polypeptide or scaffold protein to the extracellular surface, or on the outer surface of a membrane, a liposome or an exosome, or keeping the chimeric polypeptide or scaffold protein onto the extracellular surface, or on the outer surface of a membrane, a liposome or an exosome, wherein the first detectable moiety (e.g., antibody or epitope binding unit) that binds or recognizes the first epitope tag does not bind to or recognize the second epitope tag, and the second detectable moiety (e.g., antibody or epitope binding unit) that binds or recognizes the second epitope tag does not bind to or recognize the first epitope tag; wherein optionally the scaffold protein further comprises a sequence encoding a flexible peptide linker, optionally a glycine-comprising linker, optionally a four-, 5- or 6-glycine linker, optionally 1 to six repeats of a glycine linker GGGGS (SEQ ID NO:4), optionally the flexible linker is positioned between the transmembrane domain or moiety attaching the scaffold protein to the extracellular surface, or on the outer surface of a membrane, a liposome or an exosome, or keeping the chimeric polypeptide or the scaffold protein onto an extracellular surface, or on the outer surface of a membrane, a liposome or an exosome, and the membrane-proximal tag;

and optionally one of the tags comprises a FLAG tag (DYKDDDDK) SEQ ID NO:12) or an HA tag (YPYDVPDYA) (SEQ ID NO:13), and optionally further comprising a fluorescent protein positioned in the scaffold protein amino terminal to the tag distal to the cell surface, optionally the fluorescent protein comprises an mCitrine fluorescence protein.

In alternative embodiments, provided are: cells, including cell lines (optionally stable cell lines) comprising (or having contained therein) the isolated, recombinant or synthetic nucleic or chimeric acid as provided herein, or the isolated, recombinant or synthetic or chimeric polypeptide as provided herein, wherein optionally the cell is a mammalian cell, a monkey cell or a human cell, or a lymphocyte or a hepatocyte, or a T cell, and optionally the cells are genetically bar-coded. In alternative embodiments of: the cell-based method, a cell-based platform or system or a multiplexed platform or system provided herein, or the chimeric polypeptide or scaffold protein provided herein: the protease comprises or consists of, or is: a zinc-dependent proteolytic enzyme; a Matrix Metalloproteinase (MMP), or an MMP-14 protease, or a membrane-type MMP (MT-MMP), or a MT1-, MT2-, MT3-, MT4-, MT5- and MT6-MMP protease; an ADAM protein, optionally ADAM-10 (optionally a Disintegrin and metalloproteinase domain-containing protein 10) protease; or, a Neuraminidase (NA) or other viral proteins; any enzyme within the classical secretory pathway at the cell surface and/or any extracellular matrix protein (ECM), or any mammalian or human enzyme or protease, or any peptide or polypeptide having an enzyme activity or a protease-like activity, including engineered or synthetic proteins; or, the amino acid motif or subsequence susceptible to cleavage by the enzyme or protease is or comprises an amino acid motif or subsequence susceptible to cleavage by a zinc-dependent proteolytic enzyme; a Matrix Metalloproteinase (MMP), or an MMP-14 protease, or a membrane-type MMP (MT-MMP), or a MT1-, MT2-, MT3-, MT4-, MT5- and MT6-MMP protease; an ADAM protein, optionally ADAM-10 (optionally a Disintegrin and metalloproteinase domain-containing protein 10) protease; or, a Neuraminidase (NA) or other viral proteins; any enzyme within the classical secretory pathway at the cell surface and/or any extracellular matrix protein (ECM), or any mammalian or human enzyme or protease, or any peptide or polypeptide having an enzyme activity or a protease-like activity, including engineered or synthetic proteins.

In alternative embodiments, provided are: kits comprising the isolated, recombinant or synthetic, or chimeric, nucleic acid as provided herein, or vector, expression cassette, cosmid or plasmid as provided herein, or the chimeric polypeptide or scaffold protein as provided herein, or the cell, or cell line, or stable cell line as provided herein, and optionally further comprising instructions for practicing the method or multiplexed system or platform as provided herein.

Use of the isolated, recombinant or synthetic, or chimeric, nucleic acid as provided herein, or vector, expression cassette, cosmid or plasmid as provided herein, or the chimeric polypeptide or scaffold protein as provided herein, or the cell, or cell line, or stable cell line as provided herein, to practice the cell-based method, a cell-based platform or system or a multiplexed platform or system, for monitoring or assaying the activity of an enzyme or protease, of a method as provided herein.

The details of one or more embodiments of the invention are set forth in the accompanying drawings and the description below. Other features, objects, and advantages of the invention will be apparent from the description and drawings, and from the claims.

All publications, patents, patent applications, GenBank sequences cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

The drawings set forth herein are illustrative of exemplary embodiments provided herein and are not meant to limit the scope of the invention as encompassed by the claims.

FIG. 1A-B schematically illustrates exemplary assay scaffold constructs comprising two different epitope tags represented by lighter (green) and darker (red) hooks, flanking cleavable MMP-14 substrate; FIG. 1A illustrates that in the absence of MMP-14, both tags will be present at the cell surface and can be detected by antibody staining; and FIG. 1B illustrates that in the presence of MMP-14, the lighter (green) tag will be cleaved off the protein construct, leaving only the darker (red) tag at the cell surface, as described in detail in Example 1, below.

FIG. 2A schematically illustrates a short and long optimized MMP-14 substrates are introduced into a retroviral vector for mammalian expression; the MMP-14 substrates, flanked by a glycine linker, should be cleaved between the Histidine and Leucine residues; FIG. 2B schematically illustrates that as in FIG. 2A but with the addition of mCitrine fluorescent protein as marker for localization, as described in detail in Example 1, below.

FIG. 5A illustrates GFP-expressing plasmid as control; FIG. 5B illustrates a Long AHLR mCit plasmid; FIG. 5C illustrates a Short AHLR mCit plasmid; where the "green-halo" observed with the mCitrine fluorescence protein (FIG. 5B and FIG. 5C panels) in contrast to the cytosolic intracellular localization of GFP (FIG. 5A panel) corroborates that mCitrine localizes to the cell surface, as described in detail in Example 1, below.

FIG. 15A illustrates FLAG tag expression, as observed in the APC channel, is drastically reduced in the presence of MMP-14 compared to the co-transfection positive control; and FIG. 15B illustrates a co-transfection replicate experiments show that the decrease of FLAG tag in the presence of MMP-14 expression is statistically significant with p-value<0.0001 (n=4), as described in detail in Example 1, below.

FIG. 16A illustrates FLAG tag surface expression in both constitutive and inducible MMP-14 systems; FIG. 16B illustrates analysis of MMP-14(i), as observed by the expression of the coupled mNeptune fluorescent protein; FIG. 16C illustrates replicate experiments that show the decrease of FLAG surface expression upon MMP-14 induction is statistically significant with p-value<0.0001 (n=4); FIG. 16D illustrates replicate experiments that also show that the mean mNeptune fluorescence protein (indirect marker of MMP-14 expression) increases from 2.6% to 50.7% upon addition of dox, as described in detail in Example 1, below.

FIG. 17A illustrates that FLAG signal decreases upon expression of MMP-14; FIG. 17B illustrates replicate experiments that show the decrease of FLAG cell surface expression upon expression of MMP-14 is statistically significant with p-value<0.0001 (n=4). Control plasmid transfection: 84.5±2%; MMP-14 transfection: 36.1±3.3%, as described in detail in Example 1, below.

FIG. 17A illustrates replicate experiments that show the decrease of FLAG tag upon the induction of MMP-14 is statistically significant with p-value<0.05 (n=4); FIG. 17B illustrates replicate experiments that also show that the mean mNeptune fluorescence protein dramatically increased from 1.4% with no induction to 33.4% upon dox induction, as described in detail in Example 1, below.

Like reference symbols in the various drawings indicate like elements.

DETAILED DESCRIPTION

Figures 2A, 2B:
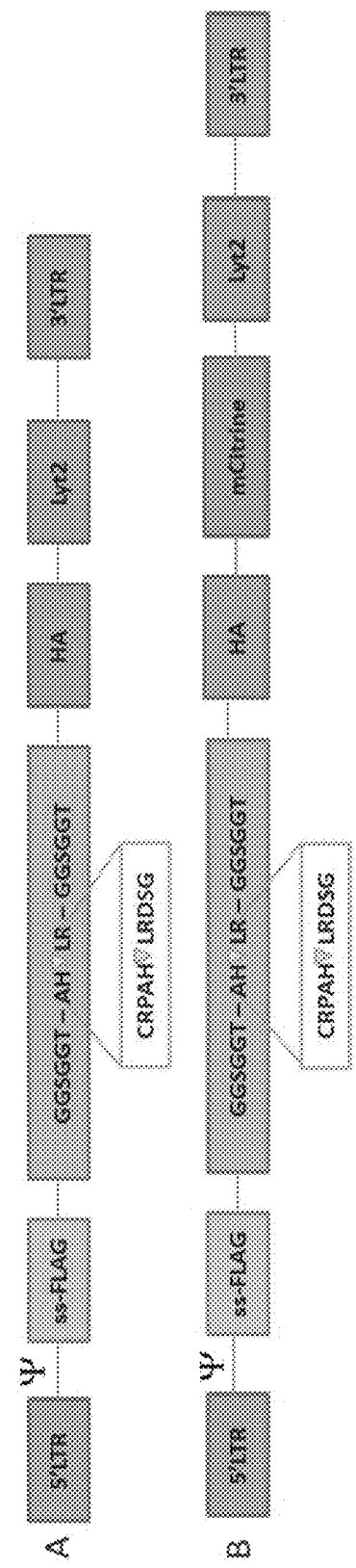
FIG. 2A-B schematically illustrates exemplary assay constructs in a retroviral plasmid.

Provided are methods and compositions, including chimeric recombinant proteins, or "scaffold proteins", the nucleic acids that encode them, and cells and kits comprising them, and multiplexed platforms or systems using them, to screen for compositions, e.g., small molecule drugs, that can modulate, e.g., inhibit or enhance, proteases, including mammalian or viral proteases. In alternative embodiments, provided are cell-based assays and multiplexed platforms or systems for the monitoring or assaying of enzyme activity such as proteolytic cleavage on the cell surface. The enzyme can be naturally expressed on the cell surface or engineered to be expressed on the cell's surface.

In alternative embodiments, methods, assays and compositions provided herein can be used for drug discovery of protease inhibitors, and also for analysis of protease substrate recognition/cleavage by the enzyme under study. In alternative embodiments, methods, assays and compositions provided herein can be used to facilitate the search for or discovery of, or confirmation of, protease inhibitors or competitors, or any other blockage agent, not only inhibitors of substrate recognition/cleavage by the enzyme. In alternative embodiments, methods, assays and compositions provided herein can be used to identify and confirm alternative recognition/cleavage sites for any protease enzyme.

An exemplary assay described herein uses MMP-14 cleavage activity as a proof-of-principle for exemplary method and composition embodiments described herein. In alternative embodiments, these assays and systems also serve as a screening tool for the search of novel MMP-14 inhibitors.

In alternative embodiments, exemplary assay, composition and method embodiments described herein are based on a two-tag system flanking an optimized substrate of the enzyme of interest, e.g., a Matrix Metalloproteinase 14 (MMP-14). In this embodiment, the two-tag system serves as the primary detection element that can distinguish cleavage and non-cleavage events, e.g., detecting the presence or absence of an inhibitor of the enzyme of interest. In one embodiment, a visually detectable marker, e.g., a fluorescent protein, is introduced adjacent to these two tags as a visual marker for cell surface localization by e.g., fluorescence microscopy or equivalent. In alternative embodiments, the entire scaffold protein is targeted to and anchored on the cell surface by the addition of an appropriate cell surface anchor, e.g., a C-terminal transmembrane domain, e.g., in the MMP-14 exemplary embodiment described herein, a mouse Lyt-2 cell surface protein C-terminal transmembrane domain.

The utility of the exemplary assay for monitoring or assaying cleavage on the cell surface is demonstrated with the overexpression of MMP-14. However, in alternative embodiments, this assay can be used as a platform to monitor or assay any cell surface proteolysis event, such as for example: cleavage of the Amyloid Precursor Protein (APP) in Alzheimer's disease (AD); proteolysis of sialic acid by the influenza virus neuraminidase (NA) for the spread of viral particles; and cleavage of HIV-1 gp-41 ectodomain by matriptase for the spread of virions. In alternative embodiments, assays provided herein are adapted to a high-throughput screening (HTS) platform for the screening for novel inhibitors of proteases responsible for a desired proteolysis event.

Here, we show that the robust proteolytic activity of MMP-14 at the cell surface coupled with a known optimized substrate of MMP-14 is exploited as a proof-of-principle to develop a novel and effective cell-based assay to monitor or assay for proteolytic cleavage events at the cell surface. In alternative embodiments, this exemplary assay is utilized as a screening tool for the search of inhibitors. While the exemplary assay presented here is specifically targeted for MMP-14, assays and methods provided herein can be used to identify any inhibitor of any enzyme when expressed on a cell surface, e.g., including other MMPs or similar enzymes that are known to cleave at the cell surface or extracellular matrix (ECM). For example, in the exemplary MMP-14 embodiment, the cell-based platforms that monitors or assays MMP-14 activity at the cell surface can identify and screen for MMP-14 inhibitors. Inhibiting the activity of MMP-14 will slow down tumor progression and metastasis, as recently shown in a preclinical model[12].

In alternative embodiments, assays provided herein comprise two elements that function in unison at the cell surface: an "assay" construct containing a putative, known or suspected substrate and a protease that recognizes it. The "assay" construct is based on a two-tag, or two-"epitope" tag, system, where the cleavable moiety (the target for the protease enzyme under study) is flanked by two different epitope tags, or equivalent.

In alternative embodiments, assays provided herein discriminate between cleaved and non-cleaved events at the cell surface or ECM. Discrimination of the two events is based on the surface antibody staining of the two epitope tags analyzed by flow cytometry. Regardless of whether cleavage or non-cleavage events occur at the cell surface, both epitope tags will be transported to the plasma membrane. In the scenario where the protease under study cleaves its substrate at the cell surface, only one tag should be detected by surface antibody staining (FIG. 1-B). On the other hand, in the scenario where no cleavage event occurs, both tags should be retained at the cell surface (FIG. 1-A). In alternative embodiments, quantitative analysis is performed through classical flow cytometry technology or equivalents. In alternative embodiments, cleavage also can be determined by microscopy or equivalents.

For example, as illustrated in FIG. 1, the schematically illustrated exemplary assay scaffold construct comprises two unique tags represented by green and red hooks, flanking cleavable MMP-14 substrate; FIG. 1A illustrates that in the absence of MMP-14, both tags will be present at the cell surface and can be detected by antibody staining; and FIG. 1B illustrates that in the presence of MMP-14, the green tag will be cleaved off the protein construct, leaving only the red tag at the cell surface.

In alternative embodiments, a flexible linker, e.g., a multi-glycine linker, e.g., a four-glycine linker, is introduced between the membrane-proximal epitope tag and the transmembrane (TM) linker, e.g., TM domain, to increase flexibility for substrate recognition at the cell surface and as a result discriminate between cleavage and lack-off by antibody staining.

Nucleic Acid Delivery—Gene Delivery Vehicles

In alternative embodiments, provided are cell-based methods, a cell-based platform or system or a multiplexed platform or system, for monitoring or assaying the activity of an enzyme or a protease extracellularly on a cell, a population of cells, or a culture of cells, or on the outer surface of a membrane, a liposome or an exosome, by transferring, transfecting, transducing, infecting or implanting one or more nucleic acids encoding an "assay" or "scaffold" protein-encoding construct as provided herein into the cell or cells (and optionally also an enzyme-encoding construct).

Any protocol, method or means of transferring, transfecting, transducing, infecting or implanting nucleic acids into cells can be used to practice embodiments as provided herein. For example, in practicing methods as provided herein, any known construct or expression vehicle, e.g., expression cassette, plasmid, vector, virus (e.g., retroviral or lentiviral expression vectors or recombinant viruses), and the like, comprising a nucleic acid encoding a readable or detectable moiety, e.g., for use as ex vivo or in vitro gene therapy vehicles, or for expression of the a readable or detectable moiety in a target cell, tissue or organ to practice the methods as provided herein, e.g., for research, diagnosis, therapy, drug discovery or transplantation.

In one aspect, an expression vehicle used to practice embodiments as provided herein can comprise a promoter operably linked to a nucleic acid encoding a readable or detectable moiety (or functional subsequence thereof). For example, embodiments as provided herein include expression cassettes comprising nucleic acid encoding a readable or detectable moiety operably linked to a transcriptional regulatory element, e.g., a promoter.

In one aspect, an expression vehicle used to practice embodiments as provided herein is designed to deliver a readable or detectable moiety encoding sequence, e.g., a fluorescent protein-encoding gene, or any functional portion thereof, to a tissue or cell of an individual. Expression vehicles, e.g., vectors, used to practice embodiments as provided herein can be non-viral or viral vectors or combinations thereof. Embodiments as provided herein can use any viral vector or viral delivery system known in the art, e.g., adenoviral vectors, adeno-associated viral (AAV) vectors, herpes viral vectors (e.g., herpes simplex virus (HSV)-based vectors), retroviral vectors, and lentiviral vectors.

In one aspect of embodiments as provided herein, an expression vehicle, e.g., a vector or a virus, is capable of accommodating a full-length gene or a message, e.g., a cDNA. In one aspect, provided are a retroviral, e.g., a lentiviral, vector capable of delivering the nucleotide sequence encoding a readable or detectable moiety in vitro, ex vivo and/or in vivo.

In one embodiment, a retroviral or a lentiviral vector used to practice embodiments as provided herein is a "minimal" lentiviral production system lacking one or more viral accessory (or auxiliary) gene. Exemplary lentiviral vectors for use in embodiments as provided herein can have enhanced safety profiles in that they are replication defective and self-inactivating (SIN) lentiviral vectors. Lentiviral vectors and production systems that can be used to practice embodiments as provided herein include e.g., those described in U.S. Pat. Nos. 6,277,633; 6,312,682; 6,312,683; 6,521,457; 6,669,936; 6,924,123; 7,056,699; and 7,198,784; any combination of these are exemplary vectors that can be employed in the practice embodiments as provided herein. In an alternative embodiment, non-integrating lentiviral vectors can be employed in embodiments as provided herein. For example, non-integrating lentiviral vectors and production systems that can be employed in embodiments as provided herein include those described in U.S. Pat. No. 6,808,923.

The expression vehicle can be designed from any vehicle known in the art, e.g., a recombinant adeno-associated viral vector as described, e.g., in U.S. Pat. App. Pub. No. 20020194630, Manning, et al.; or a lentiviral gene therapy vector, e.g., as described by e.g., Dull, et al. (1998) J. Virol. 72:8463-8471; or a viral vector particle, e.g., a modified retrovirus having a modified proviral RNA genome, as described, e.g., in U.S. Pat. App. Pub. No. 20030003582; or an adeno-associated viral vector as described e.g., in U.S. Pat. No. 6,943,153, describing recombinant adeno-associated viral vectors for use in the eye; or a retroviral or a lentiviral vector as described in U.S. Pat. Nos. 7,198,950; 7,160,727; 7,122,181 (describing using a retrovirus to inhibit intraocular neovascularization in an individual having an age-related macular degeneration); or 6,555,107.

Any viral vector can be used to practice embodiments as provided herein, and the concept of using viral vectors for gene therapy is well known; see e.g., Verma and Somia (1997) Nature 389:239-242; and Coffin et al ("Retroviruses" 1997 Cold Spring Harbour Laboratory Press Eds: J M Coffin, S M Hughes, H E Varmus pp 758-763) having a detailed list of retroviruses. Any retrovirus or lentivirus belonging to the retrovirus family can be used for infecting both dividing and non-dividing cells with a readable or detectable moiety-encoding nucleic acid, see e.g., Lewis et al (1992) EMBO J. 3053-3058.

Viruses from retrovirus or lentivirus groups from "primate" and/or "non-primate" can be used; e.g., any primate lentivirus can be used, including the human immunodeficiency virus (HIV), the causative agent of human acquired immunodeficiency syndrome (AIDS), and the simian immunodeficiency virus (SIV); or a non-primate lentiviral group member, e.g., including "slow viruses" such as a visna/maedi virus (VMV), as well as the related caprine arthritis-encephalitis virus (CAEV), equine infectious anemia virus (EIAV) and/or a feline immunodeficiency virus (FIV) or a bovine immunodeficiency virus (BIV).

In alternative embodiments, retrovirus or lentiviral vectors used to practice embodiments as provided herein are pseudotyped lentiviral vectors. In one aspect, pseudotyping used to practice embodiments as provided herein incorporates in at least a part of, or substituting a part of, or replacing all of, an env gene of a viral genome with a heterologous env gene, for example an env gene from another virus. In alternative embodiments, the lentiviral vector as provided herein is pseudotyped with VSV-G. In an alternative embodiment, the lentiviral vector as provided herein is pseudotyped with Rabies-G.

Retrovirus or lentiviral vectors used to practice embodiments as provided herein may be codon optimized for enhanced safety purposes. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available. Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms. Codon optimization has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimization also overcomes the Rev/RRE requirement for export, rendering optimized sequences Rev independent. Codon optimization also reduces homologous recombination between different constructs within the vector system (for example between the regions of overlap in the gag-pol and env open reading frames). The overall effect of codon optimization is therefore a notable increase in viral titer and improved safety. The strategy for codon optimized gag-pol sequences can be used in relation to any retrovirus.

Vectors, recombinant viruses, and other expression systems used to practice embodiments as provided herein can comprise any nucleic acid which can infect, transfect, transiently or permanently transduce a cell. In one aspect, a vector used to practice embodiments as provided herein can be a naked nucleic acid, or a nucleic acid complexed with protein or lipid. In one aspect, a vector used to practice embodiments as provided herein comprises viral or bacterial nucleic acids and/or proteins, and/or membranes (e.g., a cell membrane, a viral lipid envelope, etc.). In one aspect, expression systems used to practice embodiments as provided herein comprise replicons (e.g., RNA replicons, bacteriophages) to which fragments of DNA may be attached and become replicated. In one aspect, expression systems used to practice embodiments as provided herein include, but are not limited to RNA, autonomous self-replicating circular or linear DNA or RNA (e.g., plasmids, viruses, and the like, see, e.g., U.S. Pat. No. 5,217,879), and include both the expression and non-expression plasmids.

In one aspect, a recombinant microorganism or cell culture used to practice embodiments as provided herein can comprise "expression vector" including both (or either) extra-chromosomal circular and/or linear nucleic acid (DNA or RNA) that has been incorporated into the host chromosome(s). In one aspect, where a vector is being maintained by a host cell, the vector may either be stably replicated by the cells during mitosis as an autonomous structure, or is incorporated within the host's genome.

In one aspect, an expression system used to practice embodiments as provided herein can comprise any plasmid, which are commercially available, publicly available on an unrestricted basis, or can be constructed from available plasmids in accord with published procedures. Plasmids that can be used to practice embodiments as provided herein are well known in the art.

In alternative aspects, a vector used to make or practice embodiments as provided herein can be chosen from any number of suitable vectors known to those skilled in the art, including cosmids, YACs (Yeast Artificial Chromosomes), megaYACS, BACs (Bacterial Artificial Chromosomes), PACs (P1 Artificial Chromosome), MACs (Mammalian Artificial Chromosomes), a whole chromosome, or a small whole genome. The vector also can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook. Bacterial vectors which can be used include commercially available plasmids comprising genetic elements of known cloning vectors.

Fluorescent Proteins

In alternative embodiments, antibodies and/or epitope binding units are fluorescently tagged, and one or more fluorescent proteins are used to practice embodiments as provided herein. For example, assays of embodiments as provided herein can comprise use of one or more of: a green fluorescent protein (GFP), an Cherry protein, a td Tomato protein, an E2 Crimson protein, a Cerulean protein or an mBanana protein, or any equivalent fluorescent or otherwise detectable protein.

In alternative embodiments, a green fluorescent protein (GFP) used to practice embodiments as provided herein comprises 238 amino acid residues, at 26.9 kDa, that exhibits a bright green fluorescence when exposed to light in the blue to ultraviolet range. Equivalent green fluorescent proteins can have a major excitation peak at a wavelength of 395 nm and a minor one at 475 nm; an emission peak can be at 509 nm, which is in the lower green portion of the visible spectrum. The fluorescence quantum yield (QY) of GFP is 0.79. For example, in alternative embodiments, a GFP from the jellyfish *Aequorea victoria* or a GFP from the sea pansy *Renilla reniformis* is used having a single major excitation peak at 498 nm.

Equivalent fluorescent proteins that can be used to practice embodiments as provided herein include any red fluorescent protein, e.g., as derived from *Discosoma* sp. In one embodiment, another red fluorescent protein mCherry protein is used.

In alternative embodiments, a tdTomato used to practice embodiments as provided herein is an exceptionally bright red fluorescent protein. tdTomato's emission wavelength of 581 nm and brightness make it ideal for live animal imaging studies. The tdTomato fluorescent protein is equally photostable to mCherry.

The invention will be further described with reference to the following examples; however, it is to be understood that the invention is not limited to such examples.

EXAMPLES

Example 1: Exemplary Assays

Provided are compositions (including kits), engineered cells and cell systems, and assays, for screening for protease inhibitors.

In this exemplary embodiment, as illustrated in FIG. 1, the schematically illustrated exemplary assay scaffold construct comprises two different epitope tags represented by green and red hooks, flanking cleavable MMP-14 substrate; FIG. 1A illustrates that in the absence of MMP-14, both tags will be present at the cell surface and can be detected by antibody staining; and FIG. 1B illustrates that in the presence of MMP-14, the green tag will be cleaved off the protein construct, leaving only the red tag at the cell surface.

In this exemplary embodiment, the engineered two-tag assay "scaffold" contains the prolactin signal sequence at its N-terminus to ensure it is targeted to the ER before being transported into the plasma membrane. Downstream of the signal sequence, FLAG tag (DYKDDDDK) and HA tag (YPYDVPDYA) flank the putative substrate. Lastly, the transmembrane domain (TM) of the murine CD8a glycoprotein receptor, Lyt2, was added at the C-terminus to anchor the construct at the plasma membrane, resembling the topology of a single-pass transmembrane protein. In this exemplary embodiment, a four-, 5- or 6-glycine linker was introduced between the HA tag and TM to increase flexibility for substrate recognition at the cell surface and as a result discriminate between cleavage and lack-off by antibody staining.

For this exemplary MMP-14/MMP-14-substrate assay, four different MMP-14 substrate constructs were engineered in a Murine Leukemia Virus-based retroviral vector (pBMN). The first construct utilizes an optimized substrate of MMP-14 with an amino-acid sequence of (SEQ ID NO:1) CRPAHLRDSG[19,20] flanking short linkers (SEQ ID NO:2) (GGSGGT) as the putative substrate. For comparison, and to detect the minimal recognition/cleavage size sequence in the context of the assay, we have also engineered a short version of the optimized substrate (AHLR) (SEQ ID NO:3) with the same flanking linkers. In this construct, six repeats of the glycine linker (SEQ ID NO:4) (GGGGS) were added upstream of the HA tag to increase the distance of the substrate from the cell plasma membrane (FIG. 2A). An additional set of constructs with both 'long' and 'short' substrates include the addition of the mCitrine fluorescence protein just downstream of the HA tag (FIG. 2B) for visualization by fluorescence microscopy. For the sake of simplicity, the first two constructs will be referred as long AHLR and short AHLR, respectively, and the last two long AHLRmCit, and short AHLR mCit, respectively. FIG. 2 illustrates exemplary assay constructs in a retroviral plasmid; FIG. 2A schematically illustrates a short and long optimized MMP-14 substrates are introduced into a retroviral vector for mammalian expression; the MMP-14 substrates, flanked by a glycine linker, should be cleaved between the Histidine and Leucine residues; FIG. 2A schematically illustrates that as in FIG. 2A but with the addition of mCitrine fluorescent protein as marker for localization; LTR: Long Terminal Repeat, Ψ: packaging signal.

Figure 3:
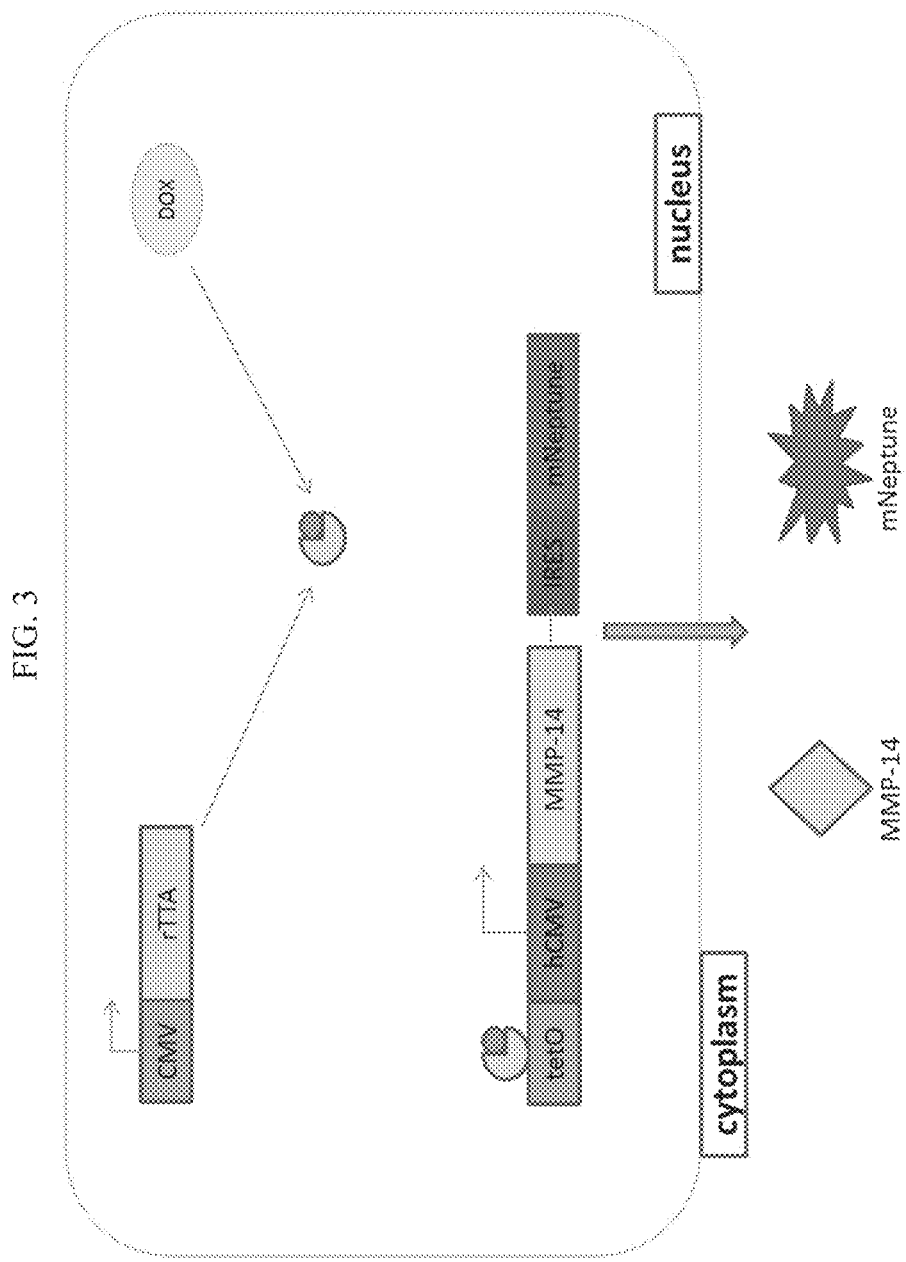
FIG. 3 schematically illustrates an exemplary tet-on MMP-14 inducible construct with mNeptune reporter protein; with the presence of doxycycline, MMP-14 and mNeptune protein will be expressed independently in an exemplary system as provided herein, as described in detail in Example 1, below.

For the expression of the MMP-14 enzyme, we have chosen two different mammalian expression systems: one for constitutive expression and the second for inducible expression. Both in retroviral vectors, for the inducible expression system MMP-14 cDNA was cloned into a tet-on system with mNeptune fluorescence reporter under an internal ribosome entry site cassette for selection based on fluorescence. Doxycycline (dox) along with the reverse tetracycline-controlled trans-activator (rtTA) protein, is used to turn on the expression of MMP-14 (FIG. 3). In the presence of dox, rtTA adopts an active conformation able to bind to the Tet Response Element (TRE) promoter and express both MMP-14 protein and mNeptune. This inducible system thus relies on two independent plasmids: rtTA and pHTRE MMP-14-IRES-mNeptune. FIG. 3 schematically illustrates an exemplary tet-on MMP-14 inducible construct with mNeptune reporter protein. With the presence of doxycycline, MMP-14 and mNeptune protein will be expressed independently in the system.

Materials and Methods

Construction of Vectors and Plasmids:

The construct pBluescript™ ssFLAG-long AHLR-HA-lyt2 was created by digesting and ligating both pBluescript SK+™ plasmid (Stratagene, Santa Clara, Calif.) and pCR-2.1 ssFLAG-long AHLR-HA-lyt2 (Eurofins, Huntsville, Ala.) with XhoI/NotI restriction enzymes. The construct pBMN ssFLAG-long AHLR-HA-lyt2 was engineered by digesting pBluescript™ ssFLAG-long AHLR-HA-lyt2 and pBMN plasmid (Nolan Lab, Stanford, Calif.) with Xho/NotI restriction enzymes, and ligating the insert into pBMN plasmid. mCitrine fluorescence protein sequence was amplified with forward primer TATAAGATCTGGCGGCTCCG-GCGTGAGCAAGGGCGAGGAG (SEQ ID NO:5), which contains a BglII site, and the reverse primer TATAGGATC-CACCGGTTTTATAGAGCTCGTCCATGCC (SEQ ID NO:6), which contains BamHI site that has compatible ends to BglII site.

The PCR product was digested with BglII and BamHI restriction enzymes, and it was ligated into pBluescript™ ssFLAG-long AHLR-HA-lyt2 that was digested with BglII restriction enzymes and treated with alkaline phosphatase in order to make pBluescript™ ssFLAG-long AHLR-HA-mCit-lyt2 construct. The construct pBMN ssFLAG-long AHLR-HA-lyt2 was engineered by digesting and ligating both pBluescript™ ssFLAG-long AHLR-HA-mCit-lyt2 and pBMN plasmid with Xho/NotI restriction enzymes. The construct pBluescript™ ssFLAG-short AHLR-HA-lyt2 and pBluescript™ ssFLAG-short AHLR-HA-mCit-lyt2 were engineered by first digesting pBluescript™ ssFLAG-long AHLR-HA-lyt2, pBluescript™ ssFLAG-long AHLR-HA-mCit-lyt2, and pBMN-short AHLR-6X glycine linker-lyt2 with EcoRI/BamHI restriction enzymes; then the resulting insert of short AHLR (SEQ ID NO:3) substrate and 6× glycine linker was ligated into the digested pBluescript™ plasmids.

The construct pBMN-ssFLAG-short AHLR-HA-lyt2 and pBMN-ssFLAG-short AHLR-HA-mCit-lyt2 were engineered by first digesting pBluescript ssFLAG-short AHLR-HA-lyt2, pBluescript ssFLAG-short AHLR-HA-mCit-lyt2, and pBMN-short AHLR-6X glycine linker-lyt2 with BamHI/NotI restriction sites; then the resulting ssFLAG-short AHLR-HA-lyt2 and ssFLAG-short-HA-mCit-lyt2 inserts were ligated into the pBMN plasmid.

The HA-tagged MMP-14 cDNA plasmid is a generous gift by Dr. Stephen J. Weiss (Weiss Lab, Ann Arbor, Mich.). In order to clone HA-tagged MMP-14 cDNA into an inducible expression plasmid, pHTRE-IRES-mNeptune, two set of primers are used to amplify MMP-14 cDNA. The forward TATATAGAATTCCCACCATGTCTCCCGC-CCCAAGACCC (SEQ ID NO:7) primer has an 5' EcoRI site, and the reverse TATATAGCTAGCTCAGACCTTGTC-CAGCAGGGAACG (SEQ ID NO:8) primer has a 3' NheI site. PCR products of MMP-14 cDNA and pHTRE-IRESmNeptune were digested with EcoRI and NheI restriction enzymes and ligated to make pHTRE-MMP-14-IRES-mNeptune construct.

Transfection for transient expression: A 12-well plate of HEK 293 cells at 70-80% confluence was transfected with 1 µg of the assay construct plasmids (pBMN-long-AHLR, pBMN-short-AHLR, pBMN-long-AHLR-mCit, pBMN-short-AHLR-mCit) or 1 µg of HA-tagged MMP-14 plasmid in cell surface localization experiments. For assay validation experiment, cells at the same confluence were transfected with 750 ng of the assay construct plasmids for single expression, or they are transfected with 750 ng of the assay construct plasmids and 1 µg HA-tagged MMP-14 plasmid for co-expression.

For the inducible system transfection experiment, 750 ng of the assay construct plasmid, 750 µg of HA-tagged MMP-14 plasmid, and 500 ng of rtTA plasmid were transfected in HEK 293T cells. With cell lines expressing AHLR (SEQ ID NO:3), 1 µg of HA-tagged MMP-14 plasmid and 500 ng of rtTA plasmid were transfected to test the inducible system. For both transfection conditions, dox was added to a final concentration of 4 µg/mL in order to induce transient expression of HA-tagged MMP-14.

Transfection was done by mixing the plasmids and Polyethylenimine (PEI) max with the ratio of 8 µL of PEI max per 1 µg of total DNA (linear, MW 40000; Polysciences, Inc, Warrington, Pa.) in 100 µL FBS-free DMEM separately. After 5 minutes incubation, PEI max solution was added into the DNA solutions, and the mixtures are incubated for 15 minutes at room temperature (RT). The mixtures were then added into the cells in a drop-wise manner. After 48 hours incubation, the cells are analyzed on flow cytometry or fluorescence microscope.

Flow Cytometry Analysis and Sorting:

Cells were pelleted and incubated with mouse anti-FLAG and/or mouse anti-HA (Sigma Aldrich, St. Louis, Mo.) at 1:400 dilution for 1 hour at room temperature (RT). Cells were then washed three times with Phosphate Buffer Saline (PBS) without Calcium or Magnesium. Cells were then incubated with anti-mouse Alexa Fluor 488 or 647 at 1:400 dilutions for 30 minutes in a dark condition. Cells were washed three more times with PBS before being analyzed via flow cytometry. Flow cytometry analysis was performed on a BD FACSCanto™ with 488-nm (FITC) and/or 647-nm (APC) lasers, and flow analysis cell sorting (FACS) was performed on BD FACSAria™ with APC laser. Data was collected on FACSDiva 6.1.1™ and analyzed using FlowJo 7.6.5™.

Fluorescence Microscopy:

Cells were checked for fluorescence on a Zeiss Observer D1 microscope with a 50× lens connected to an AxioCam MRm™ camera, and analyzed on Axio-Vision™ software.

Cell Maintenance:

Human Embryonic Kidney (HEK) 293T cell line and Phoenix GP packaging cell line were obtained from Dr. Gary Nolan (Nolan Lab, Stanford University, CA). Cells were maintained in complete Dulbecco's Modified Eagle's Media supplemented with 10% fetal bovine serum (Gemini Bio-Products, West Sacramento, Calif.), glutamine (2 mM), penicillin G (100 units/mL), and streptomycin (100 µg/mL).

Viral production and transduction: For the production of Moloney murine leukemia virus (MMLV)-based retrovirus, a 8 cm$^2$ plate of Phoenix GP cells at 70% confluence were transfected with 2.5 µg of the AHLR plasmid (pBMN transfer plasmid) and 2.5 µg of pCI-VSVg (envelope plasmid). Transfection was done by mixing the DNA in 500 µl of serum free (SF) DMEM with 40 µL of PEI MAX™ (linear, MW 40000; Polysciences, Inc, Warrington, Pa.).

For the MMLV-based viral production, complete media (DMEM with 10% FCS, Pen-Strep, L-Glutamine) was replaced 24 hours post-transfection and viral supernatant was collected 48 and 72 hours after transfection and filtered through 0.45 micron polytetrafluoroethylene (PTFE) filters (Pall Corporation). The viral supernatant was then mixed with polybrene (5 ug/mL final concentration) and used to infect naïve HEK293T cells at 30% confluency in a well of a 6 well-plate. After 24 hours, viral supernatant was replaced with 2 mL fresh complete media.

Western Blotting:

293T cells of interest were lysed in modified RIPA buffer (150 mM NaCl, 20 mM Tris pH 7.5, 1% Triton X-100, 0.1% SDS) supplemented with Complete Protease Inhibitor cocktail (Roche, Indianapolis, Ind.) on ice for 30 min. Cellular extracts centrifuged at 13,000 g for 10 min. The supernatant fraction was then boiled in Laemmli's loading buffer with 8% BME at 100° C. for 5 min and run on 10% SDS-PAGE Tris-Glycine gels at 120V for 90 minutes. Proteins were transferred to PVDF membranes at 15V overnight. Membranes were blocked with 5% milk in PBST (PBS+ 0.05% Tween 20) at pH 7.5 (with 1M HCl) for 1 hour at room temperature (RT). The primary rabbit HA (Cell Signaling) antibody were diluted to 1:1000 in 5% milk and incubated at 4° C. overnight. Secondary rabbit IgG antibodies conjugated to HRP (Cell Signaling) were added at 1:2000 dilution in 5% milk for 30 minutes. Membranes were washed in PBST three times for 5 min at RT following primary and secondary antibody staining. Antibody staining was detected by an ENHANCED CHEMILUMINESCENCE™ kit (Pierce) and exposed at varying time points in auto-radiography film (Genesee Scientific, San Diego, Calif.) in a dark room.

Results

Figure 4:
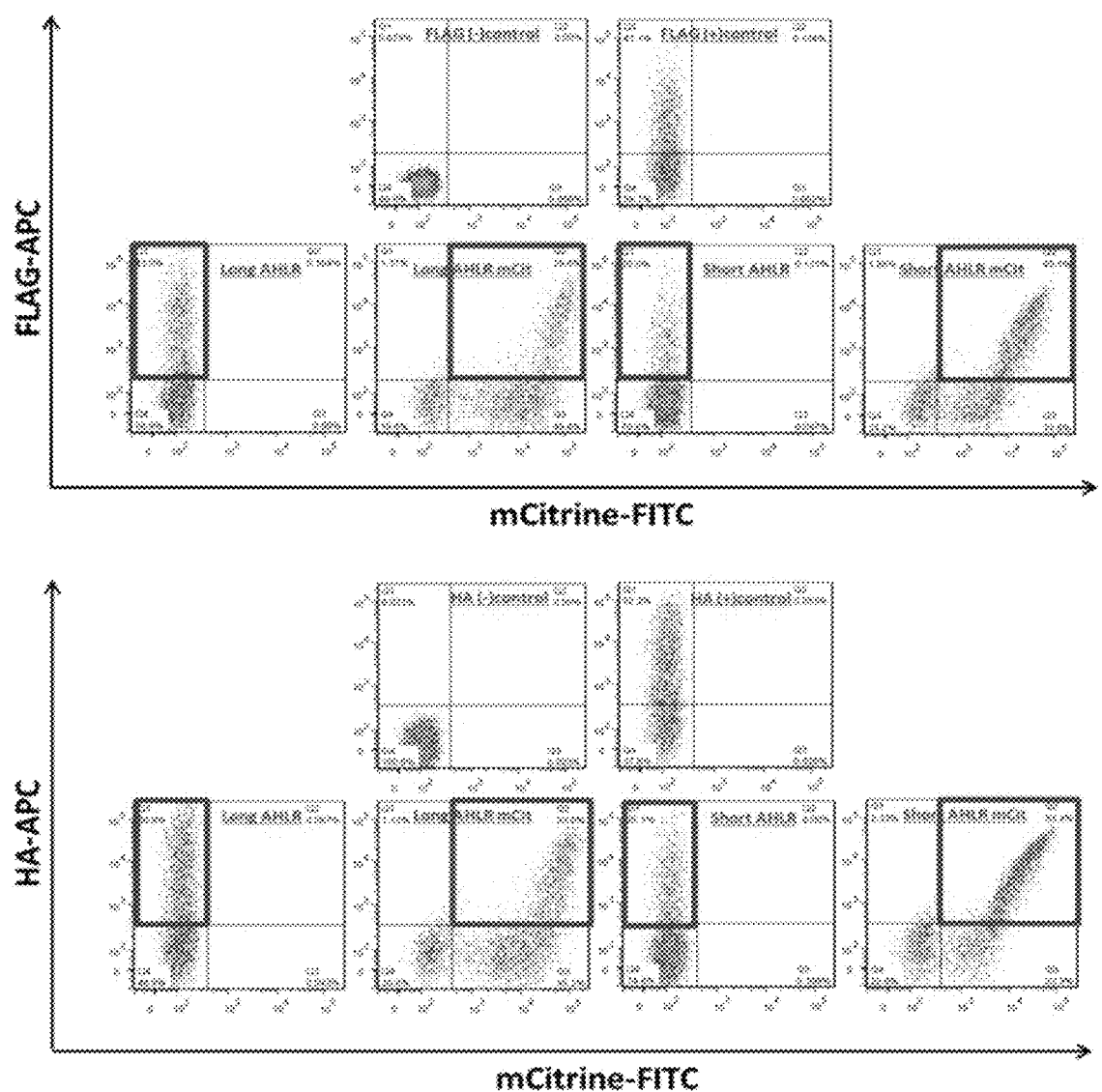
FIG. 4 graphically illustrates data from a flow analysis of 293T cells transfected with four exemplary AHLR constructs; FLAG (upper panel) and HA (lower panel) staining both showed detection of both tags on the cell surface of transfected cells, as described in detail in Example 1, below.
Figure 7:
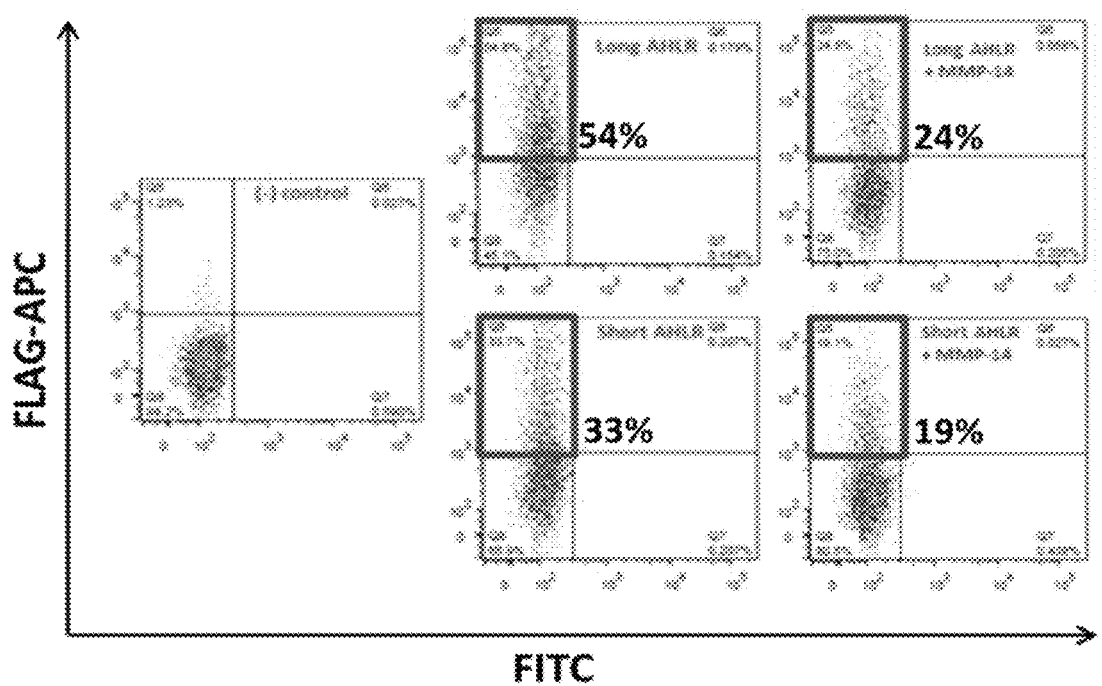
FIG. 7 graphically illustrates data from a flow cytometry analysis of cells expressing both an exemplary assay (left panel is negative control) and MMP-14: FLAG tag expression, as observed in the APC channel, is drastically reduced in the presence of MMP-14 with both short and long MMP-14 substrates: flow cytometry analysis clearly shows that both HA and FLAG tags are highly detected at the cell surface in cells transfected with each of the four AHLR constructs, and a significant shift in the HA-APC axis compared to the naïve 293T cells was observed: 51%, 34%, 25%, and 55%, for long AHLR, long AHLR mCit, short AHLR, and short mCit AHLR respectively (FIG. 7, lower panels on right); and a significant shift in the FLAG-APC axis was also observed: 43%, 30%, 20%, and 46% increase respectively (FIG. 7, upper panels on right), as described in detail in Example 1, below.

Substrate Cell Surface Localization—Flow Cytometry Analysis:

In order to test that the substrate-bearing constructs travel to the cell surface, HEK 293T cells were transfected with each of the four individual constructs and stained 48 hours post-transfection with anti-HA or anti-FLAG tag antibodies and APC-fluorophore-conjugated secondary antibody. Flow cytometry analysis clearly shows that both HA and FLAG tags are highly detected at the cell surface in cells transfected with each of the four AHLR constructs. A significant shift in the HA-APC axis compared to the naïve 293T cells is observed: 51%, 34%, 25%, and 55%, for long AHLR, long AHLR mCit, short AHLR, and short mCit AHLR respectively (FIG. 7, lower panels). A significant shift in the FLAG-APC axis was also observed: 43%, 30%, 20%, and 46% increase respectively (FIG. 7, upper panels). Furthermore, cells transfected with the constructs bearing the mCitrine protein, long AHLR mCit or short AHLR mCit, show a drastic shift in the FITC channel: 78% and 76%, respectively (FIG. 4, both panels). FIG. 4 graphically illustrates a flow analysis of 293T cells transfected with the four AHLR constructs. FLAG and HA staining both showed detection of both tags on the cell surface of transfected cells. These results demonstrate that the four AHLR substrate constructs are not only highly expressed, but importantly, are also translocated onto the cell surface.

Substrate Cell Surface Localization—Fluorescence Microscopy Analysis:

To corroborate the cell surface localization of the substrate constructs, we utilized fluorescence imaging technique to visualize the constructs harboring the mCitrine protein.

Figure 5A:
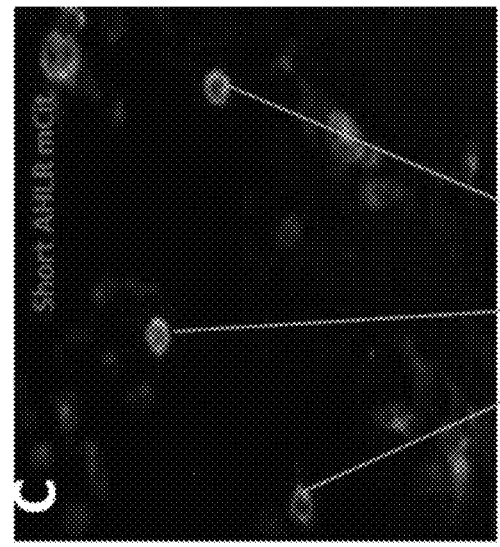
FIG. 5A-C illustrates images of a fluorescence microscopy analysis of 293T cells transfected with AHLR mCit constructs.
Figure 5B:
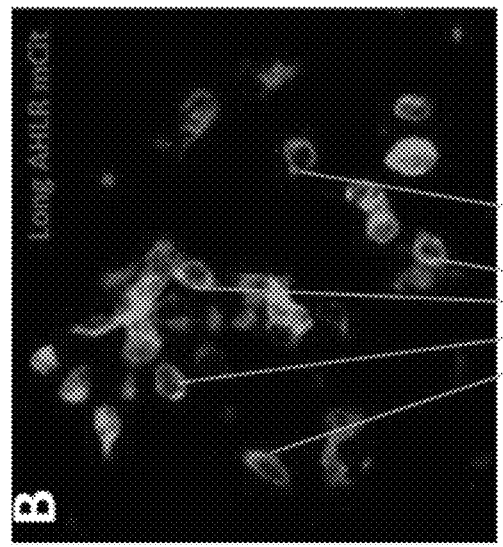
Figure 5C:
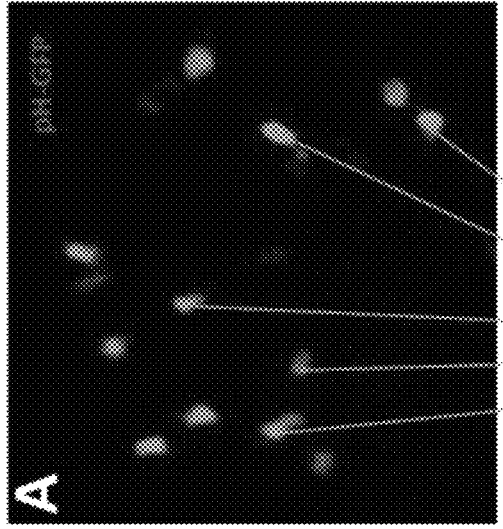

For that purpose, HEK 293T cells transfected with either long AHLR mCit or short AHLR mCit were analyzed by fluorescence microscopy 48 hours post-transfection. Cells transfected with a plasmid bearing the Green Fluorescence Protein (GFP) gene was used as control. The "green-halo" observed with the mCitrine fluorescence protein (FIGS. 5B and 5C panels) in contrast to the cytosolic intracellular localization of GFP (FIG. 5A panel) corroborates that mCitrine localizes to the cell surface. FIG. 5 illustrates a fluorescence microscopy analysis of 293T cells transfected with AHLR mCit constructs. FIG. 5A. GFP-expressing plasmid as control. FIG. 5B. Long AHLR mCit plasmid. FIG. 5C. Short AHLR mCit plasmid.

Both fluorescence microscopy and flow cytometry analyses thus corroborate that the AHLR products translocate and localize to the cell surface. This is crucial as the assay is intended to monitor or assay cleavage activity at the cell surface.

Figure 6:
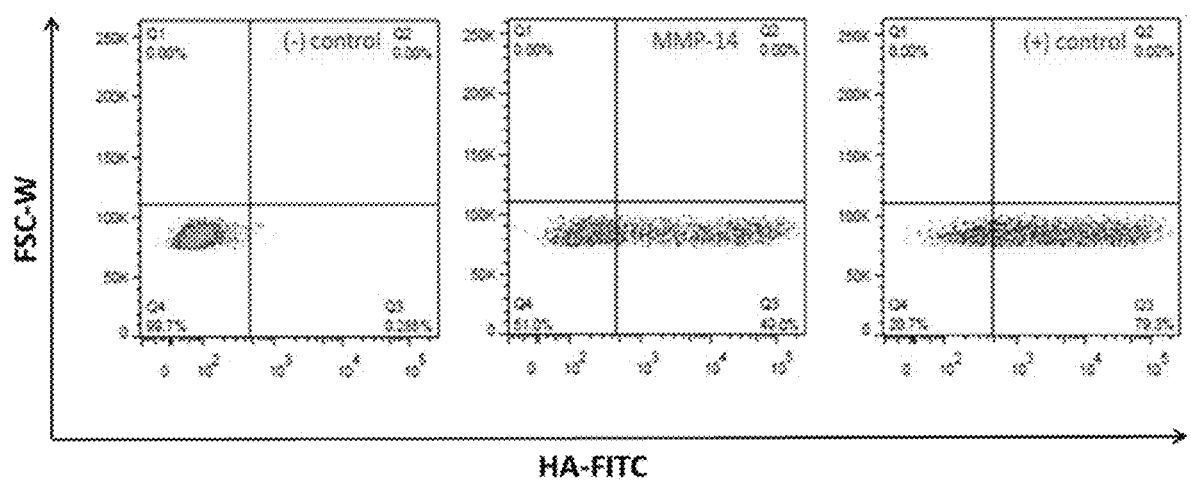
FIG. 6 graphically illustrates data from a low cytometry analysis of MMP-14 cell surface expression: an HA-tagged MMP-14 protein (center panel), expressed from a mammalian expression plasmid (right panel positive control), was detected on the cell surface by anti-HA antibodies; a significant shift in the HA-FITC channel was observed in cells expressing the HA-tagged-MMP-14 compared to naïve untransfected cells (left panel), confirming that MMP-14 is expressed and localized on the cell surface, as described in detail in Example 1, below.

MMP-14 Cell Surface Localization—Flow Cytometry Analysis:

Following confirmation of the proper expression and localization of the AHLR substrates, it was critical to evaluate the expression and localization of the MMP-14 enzyme. Full-length human MMP-14 cDNA was engineered into a mammalian expression vector with an HA-tag upstream of the MMP-14 transmembrane domain. HEK 293T cells were transfected with HA tagged-MMP-14 plasmid and analyzed by flow cytometry 48 hours post-transfection following anti-HA and FITC fluorophore-conjugated secondary antibody staining. A significant shift in the HA-FITC channel was observed in cells expressing the HA-tagged-MMP-14 compared to naïve un-transfected cells (FIG. 6), confirming that MMP-14 is expressed and localized on the cell surface. FIG. 6 graphically illustrates a low cytometry analysis of MMP-14 cell surface expression: an HA-tagged MMP-14 protein, expressed from a mammalian expression plasmid, was detected on the cell surface by anti-HA antibodies.

The Assay—Monitoring or Assaying Proteolysis:

After confirming that both substrate (AHLR constructs) and enzyme (MMP-14 protease) are localized on the cell surface, it was necessary to express both elements simultaneously in order to evaluate the utility of the assay. For that purpose, HEK 293T cells were co-transfected with both the MMP-14 plasmid and either long AHLR or short AHLR constructs. Transfection of AHLR constructs alone (without MMP-14) was performed in parallel as a negative control. 48 hours post-transfection cells were analyzed by flow cytometry following anti-FLAG tag and APC-fluorophore-coupled secondary antibody staining. A clear reduction in FLAG tag expression was indeed observed in cells expressing both substrate and enzyme compared to those expressing just the substrate: the long AHLR constructs showed a 54% to 24% decrease was observed with the long AHLR constructs, and a 33% to 19% decrease with the short AHLR constructs (FIG. 7). FIG. 7 graphically illustrates a flow cytometry analysis of cells expressing both the assay and MMP-14. FLAG tag expression, as observed in the APC channel, is drastically reduced in the presence of MMP-14 with both short and long MMP-14 substrates.

This experiment reveals a clear loss of FLAG tag cell surface expression in the presence of MMP-14, most probably due to the proteolysis of the AHLR substrate by MMP-14. Interestingly, the longer substrate seems to be better expressed (or detected) and cleaved at a higher rate than the shorter substrate, at least in transient expression experiments. The long AHLR substrate, which includes several amino acids flanking the cleavage site (histidine/leucine boundary, was thus used in all subsequent experiments, and referred to as just AHLR.

Figure 8:
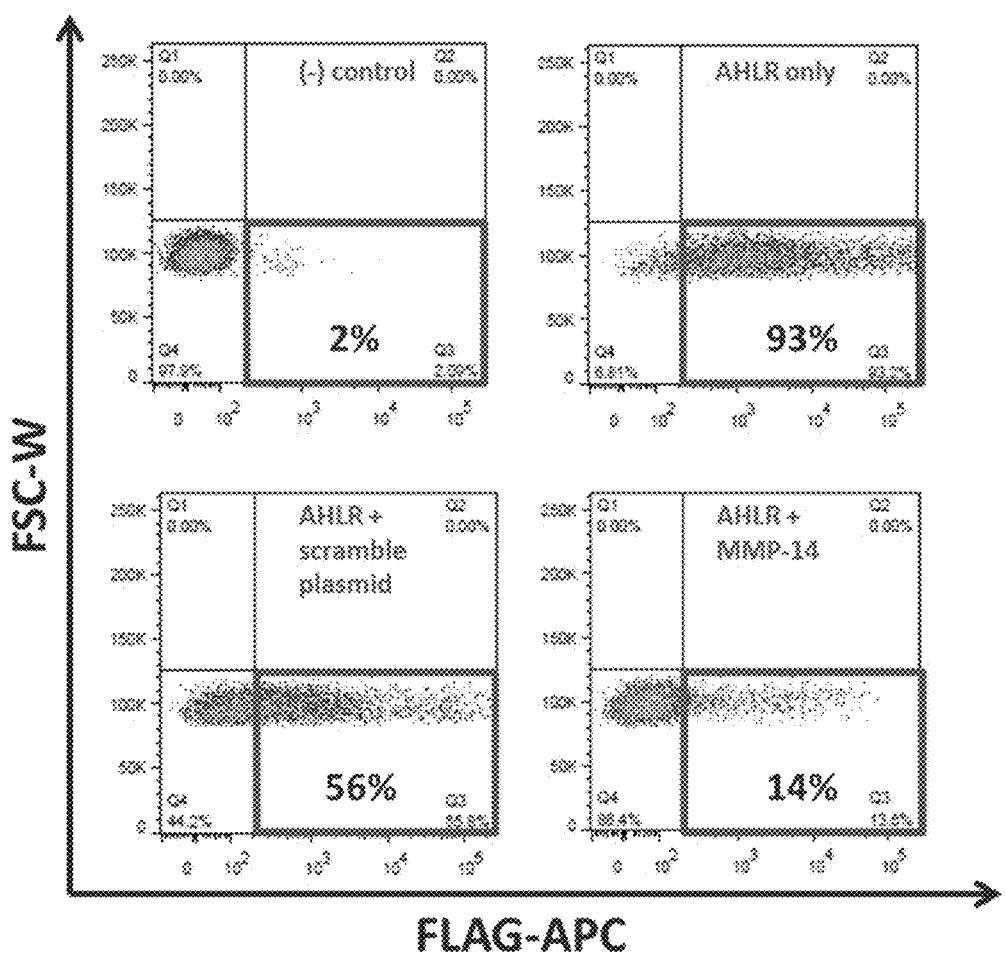
FIG. 8 graphically illustrates data from a flow cytometry analysis of cells expressing AHLR and MMP-14 or negative control (upper left panel) plasmid: FLAG tag expression, as observed in the APC channel, is drastically reduced in the presence of MMP-14 compared to the co-transfection positive control; and the presence of MMP-14 led to a 56% to 14% decrease in FLAG cell surface detection, as described in detail in Example 1, below.

In order to corroborate that the decrease in FLAG tag cell surface expression is due to the presence of MMP-14 and not an artifact of protein expression or transfection of one versus two plasmids, we performed an additional co-transfection experiment. AHLR in the presence of MMP-14 was compared to AHLR in the presence of a control plasmid. Flow cytometry analysis showed a decrease from 93% to 56% in FLAG-cell surface expression when AHLR was co-transfected with a second control plasmid. Importantly, however, co-transfection of AHLR with MMP-14-carrying plasmid showed a further significant decrease of the FLAG tag signal to 14%. In short, and taking into account the reduced efficiency in co-transfection experiments, the presence of MMP-14 led to a 56% to 14% decrease in FLAG cell surface detection (FIG. 8), further suggesting cleavage of AHLR by MMP-14 in the context of the assay. FIG. 8 graphically illustrates Flow cytometry analysis of cells expressing AHLR and MMP-14 or negative control plasmid. FLAG tag expression, as observed in the APC channel, is still drastically reduced in the presence of MMP-14 compared to the co-transfection positive control.

Figure 9:
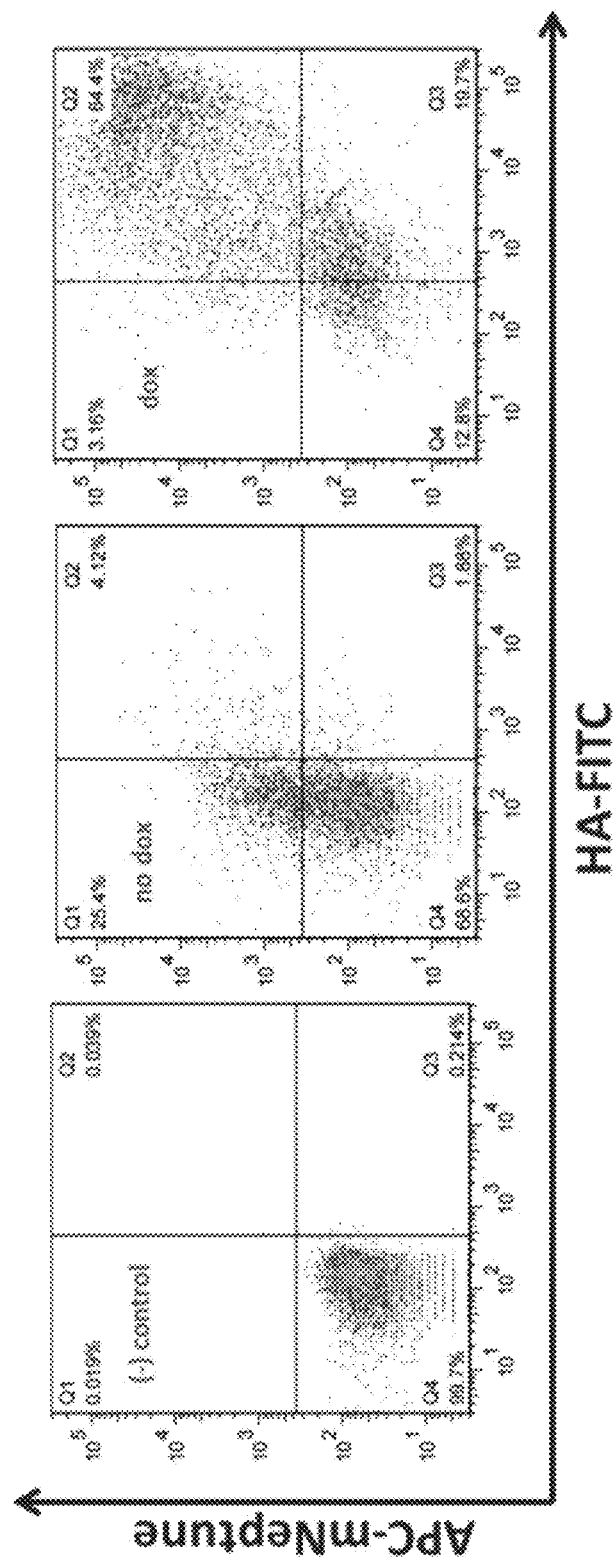
FIG. 9 graphically illustrates data from a flow cytometry analysis of an exemplary inducible MMP-14 system provided herein, where flow cytometry analysis shows a drastic increase (6% to 67%) of the double-positive FITC (MMP-14) and APC (mNeptune) channels upon induction with dox, corroborating the inducibility of MMP-14, as described in detail in Example 1, below.

Analysis of Inducible MMP-14 Expression:

Tet-on inducible MMP-14 expression was engineered to further confirm the ability of the assay to monitor or assay cleavage in the context of the assay and to specifically demonstrate that cleavage of the AHLR substrate was performed by MMP-14. If cleavage of the AHLR substrate is indeed performed by MMP-14, a reduction of the FLAG-tag signal should be observed only when the MMP-14 protein expression is turned on by the addition of dox. We first tested the inducibility of MMP-14 by transfecting the pHTRE-MMP-14-IRES-mNeptune plasmids into HEK 293T cells we have previously engineered to express the rtTA protein. Anti-HA and FITC fluorophore-conjugated secondary antibody staining was used to detect the HA-tagged MMP-14 protein. Flow cytometry analysis shows a drastic increase (6% to 67%) of the double-positive FITC (MMP-14) and APC (mNeptune) channels upon induction with dox (FIG. 9), corroborating the inducibility of MMP-14. FIG. 9 graphically illustrates flow cytometry analysis of inducible MMP-14 system. The expression of both MMP-14 and mNeptune fluorescence protein are much higher with the addition of dox, highlighting the inducibility property of the system.

Figure 10:
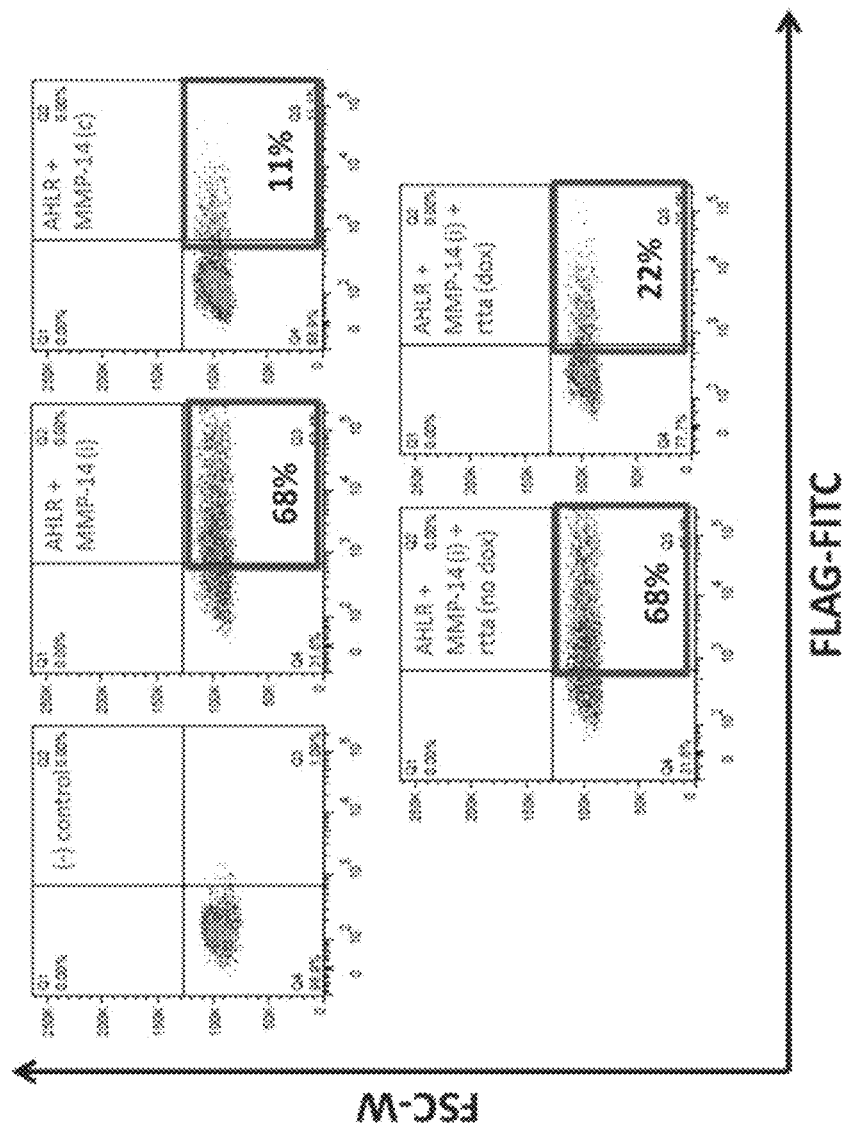
FIG. 10 graphically illustrates data from a flow cytometry analysis of the exemplary MMP-14(i) (middle upper panel, lower two panels) and the exemplary MMP-14(c) (upper right panel) exemplary expression systems in an exemplary assay (control assay is upper left panel): a decrease of FLAG tag signal was observed in the assay upon the expression of either constitutive or inducible MMP-14, as described in detail in Example 1, below.

Analysis of Inducible MMP-14 Expression in the Context of the Assay:

An inducible system for MMP-14 allowed us to further analyze the effects of MMP-14 in the context of the assay. We thus aimed at comparing the inducible and constitutive expression of MMP-14 in the presence of the AHLR substrate. For the sake of simplicity, the inducible MMP-14 expression plasmid was referred to as MMP-14 (i) whereas the constitutive MMP-14 expression plasmid would be referred to as MMP-14 (c). For the inducible system, HEK-293T cells were co-transfected with AHLR substrate, MMP-14 (i) and rtTA. We observed a decrease in FLAG tag signal from 68% to 22% upon dox induction. This decrease was comparable to the decrease observed in the constitutive-expression experiment (68% to 11%) (FIG. 10). FIG. 10 graphically illustrates a flow cytometry analysis of MMP-14 (i) and MMP-14 (c) expression system in the assay. A decrease of FLAG tag signal was observed in the assay upon the expression of either constitutive or inducible MMP-14.

This exemplary inducible system further demonstrated that MMP-14 is most likely the "culprit" protease responsible for the decrease in FLAG signal.

Figure 11:
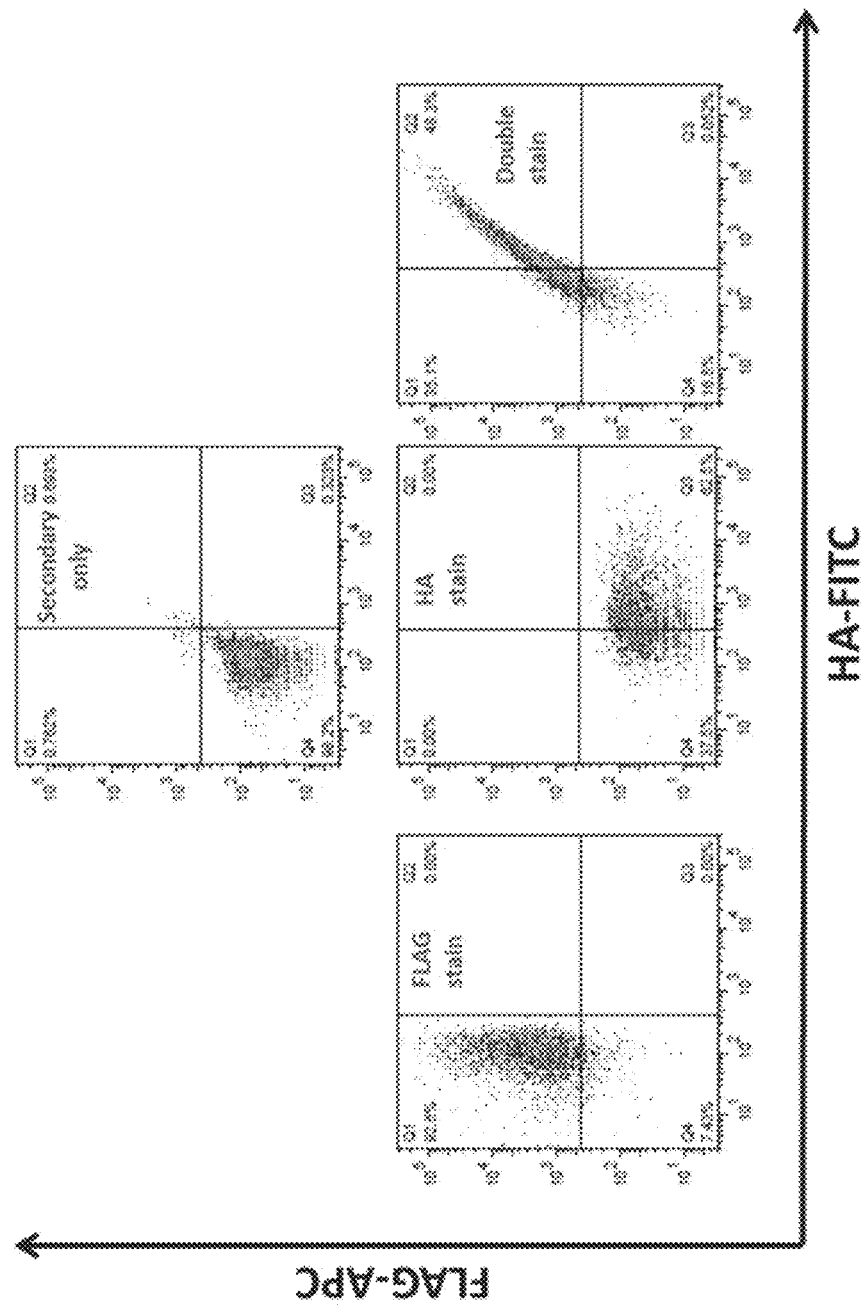
FIG. 11 graphically illustrates data from a flow cytometry analysis of AHLR+ cells in the context of an exemplary assay: FLAG tag signal decreases after an overexpression of MMP-14 in the AHLR+ cells, as described in detail in Example 1, below.

Stable Cell-Lines Harboring the Assay:

Previous experiments were performed with transient protein expression in HEK 293T transfected cells. In order to obtain a robust mammalian cell-based assay that consistently and robustly expresses the assay, we exploited the power of retroviral technology (see 'methods' section). A retroviral plasmid carrying the AHLR substrate (pBMN-ssFLAG-AHLR-HA-lyt2) was utilized to obtain AHLR+ cells stably expressing the substrate. For that purpose, HEK 293T cells transfected with retroviral particles were analyzed by Fluorescence-activated Cell Sorter (FACS) and sorted based on FLAG surface expression (positive for FLAG-APC). An enriched sorted cell population was analyzed by flow cytometry following HA and FLAG staining as previously described. AHLR+ cells express high levels of both HA (63%) and FLAG (93%) (FIG. 11) as compared to control naïve HEK 293T cells. The lower HA signal is most probably due to staining conditions and/or antibody quality. FIG. 11 graphically illustrates a flow cytometry analysis of AHLR+ cells. AHLR+ cells are positive for FLAG tag and HA tag which suggests the expression of AHLR construct.

Proteolysis Analysis of Cells Expressing the MMP-14 Substrate:

In order to verify the AHLR+ cells can be used to monitor or assaying for cleavage by MMP-14, we further tested them in a transfection experiment with MMP-14. Naïve, untransfected AHLR+ cells and empty control plasmid-transfected AHLR+ cells were used as background controls. Flow cytometry analysis following FLAG-tag staining showed high level AHLR substrate expression (77%), which was drastically reduced to 23% when transfected with the MMP-14(c) plasmid. Therefore, proteolysis by MMP-14 could be clearly detected in the stable cell line platform (AHLR+ cells), as observed with the non-stably substrate-expressing cells. FIG. 11 graphically illustrates a flow cytometry analysis of AHLR+ cells in the context of the assay. FLAG tag signal decreases after an overexpression of MMP-14 in the AHLR+ cells.

Figure 12:
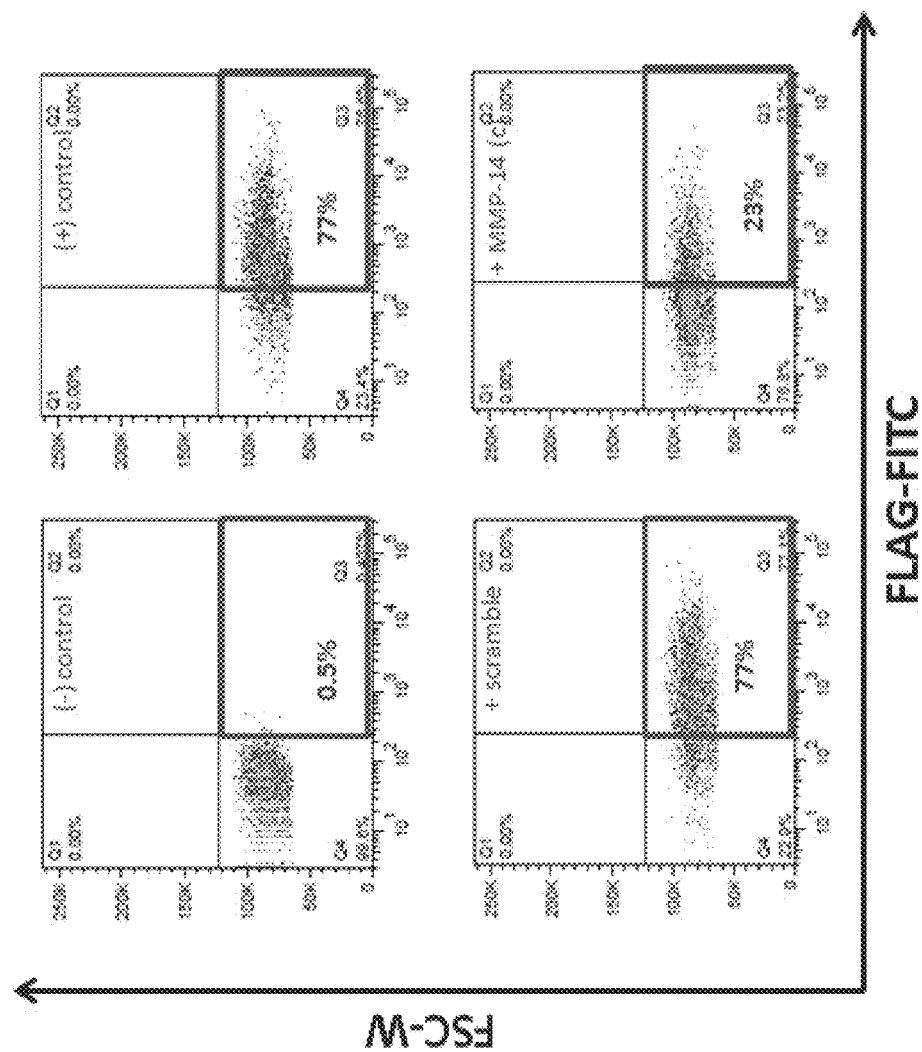
FIG. 12 graphically illustrates data from a flow cytometry analysis of AHLR+ cells in the context of an exemplary assay: FLAG tag signal decreases after an overexpression of MMP-14 in the AHLR+ cells, as described in detail in Example 1, below.

We then proceeded to prove the utility of the AHLR+ cells for monitoring or assaying cleavage by MMP-14. Again, as shown in FIG. 12, transfection of AHLR+ cells with the constitutive MMP-14(c) led to a drastic decrease in the FLAG-tag signal (92% to 33%) (FIG. 16, panel A). Surprisingly, transfection of AHLR+ cells with inducible MMP-14 (i) revealed a significant loss of FLAG-tag signal (92% to 56%) even in the absence of dox, and a further decrease to 38% upon the addition of dox. While the system seemed leaky, a similar decrease in FLAG-tag signal was observed with both constitutive and inducible MMP-14 expression (33% and 38%, respectively). Interestingly, upon expression of MMP-14, the FLAG-tag signal seems slightly higher in AHLR+ cells than in co-transfection experiments. This might be expected due to the stable expression and continuous translocation of the AHLR substrate to the cell surface, prior and during the expression of MMP-14. Thus, the AHLR+ cells have to be further optimized, probably by selecting for clonal AHLR+ populations expressing low AHLR levels rather than utilizing a mixed population of AHLR+ cells with different substrate expression levels. FIG. 12 graphically illustrates a flow cytometry analysis of AHLR+ cells in the context of the assay. FLAG tag signal decreases after an overexpression of MMP-14 in the AHLR+ cells.

Figure 13:
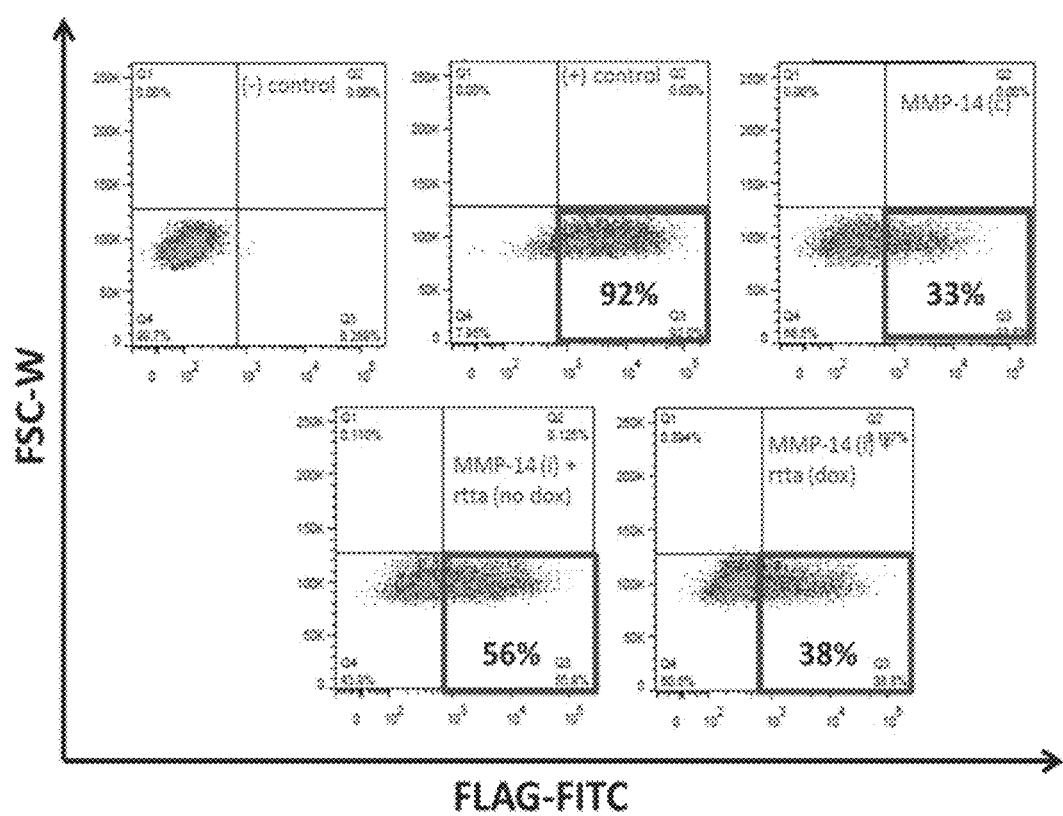
FIG. 13 graphically illustrates data from a flow cytometry analysis of AHLR cells with the exemplary MMP-14(c) and MMP-14(i): FLAG tag signal decreases upon the expression of MMP-14, as described in detail in Example 1, below.

We then proceeded to prove the utility of the AHLR+ cells for monitoring or assaying cleavage by MMP-14. Again, as shown in FIG. 12, transfection of AHLR+ cells with the constitutive MMP-14(c) led to a drastic decrease in the FLAG-tag signal (92% to 33%) (FIG. 13, upper right panel). Surprisingly, transfection of AHLR+ cells with inducible MMP-14(i) revealed a significant loss of FLAG-tag signal (92% to 56%) even in the absence of dox, and a further decrease to 38% upon the addition of dox. While the system seemed leaky, a similar decrease in FLAG-tag signal was observed with both constitutive and inducible MMP-14 expression (33% and 38%, respectively). Interestingly, upon expression of MMP-14, the FLAG-tag signal seems slightly higher in AHLR+ cells than in co-transfection experiments. This might be expected due to the stable expression and continuous translocation of the AHLR substrate to the cell surface, prior and during the expression of MMP-14. Thus, the AHLR+ cells have to be further optimized, probably by selecting for clonal AHLR+ populations expressing low AHLR levels rather than utilizing a mixed population of AHLR+ cells with different substrate expression levels. FIG. 13 graphically illustrates a flow cytometry analysis of AHLR cells with MMP-14 (c) and MMP-14 (i). FLAG tag signal decreases upon the expression of MMP-14.

Figure 14:
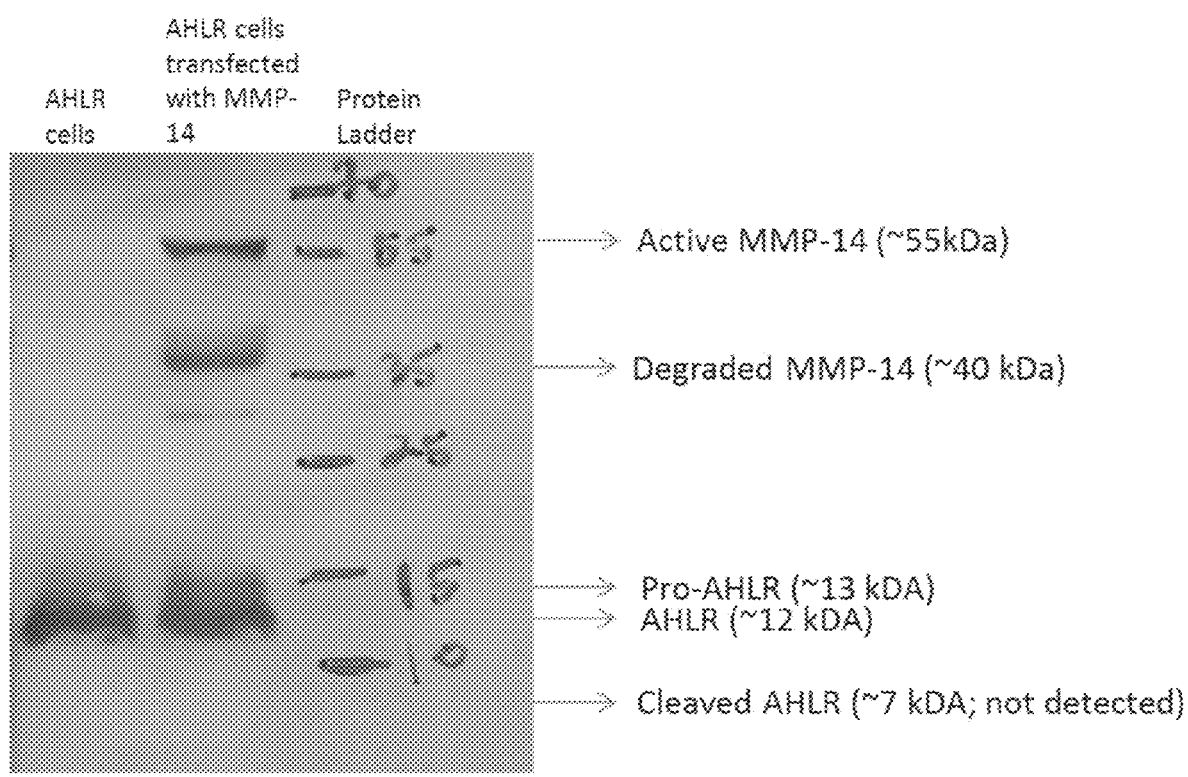
FIG. 14 illustrates an image of an immunoblot of AHLR cells with the overexpression of MMP-14. Active and degraded forms of MMP-14 are observed in MMP-14 positive AHLR cells; protein ladder markers are from bottom to top: 10, 15, 25, 35, 55 and 75 kD, as described in detail in Example 1, below.

Western Blot Analysis of Cells Expressing the MMP-14 Substrate:

While flow cytometry can assess expression of substrate and enzyme at the cell surface and further cleavage in a robust and high throughput manner, it is important to corroborate cleavage in a classical biochemical approach. Western blot was performed to provide another solid evidence of MMP-14 cleavage in the assay; FIG. 14 illustrates an immunoblot of AHLR cells with the overexpression of MMP-14. Active and degraded forms of MMP-14 are observed in MMP-14 positive AHLR cells. However, cleaved AHLR product is not detected in that same extract. A cleavage event should be observed in immunoblotting based on the slight size difference between uncleaved AHLR (approximately 13 kDA) and cleaved AHLR (approximately 7 kDA) protein construct. For that purpose, AHLR+ cells were transfected with MMP-14 (c), and utilized to protein extracts. SDS-PAGE stained with HA antibody show (FIG. 14) clear expression of MMP-14 (active MMP-14 and degraded MMP-14) as compared to naïve AHLR cells, demonstrating efficient expression of MMP-14. Nascent MMP-14 of around 64 kDA in size was not detected most likely because the majority of nascent MMP-14 is already cleaved into its active 55 kDA protein form. Furthermore, a solid band and a faint band around 40-44 kDA appeared in the MMP-14 transfected AHLR+ cells, but not in naïve AHLR+ cells. These bands are presumably thought to be degradation products of MMP-14. MMP-14 is thought to possess a down-regulation mechanism by the removal of its catalytic domain via auto-proteolysis at the cell surface. This degraded or auto-cleaved MMP-14 is then recycled back into the cell for further degradation processing[34].

Bands around 11-13 kDA appeared in both lanes revealing the presence of the AHLR substrate protein in AHLR+ cells. A fainter band around 13 kDA is probably representative of pro-AHLR nascent protein in which prolactin signal sequence has not yet been cleaved in the Endoplasmic Reticulum (ER) by signal peptidases. The more solid band around 12 kDA is probably AHLR protein following the cleavage of the prolactin signal sequence by pro-protein convertase. A 7 kDA expected band of the cleaved AHLR product was not observed in the MMP-14 co-transfected cells probably due it is too small size. Conversely, it might not been dissolved within the protein extract due to its association with cell (ER) membranes.

Stable Cell Lines Expressing Assay Elements of the Assay:

In order to ensure consistent and robust expression of both substrate and enzyme, provided are stable cell lines expressing not only the long AHLR substrate construct but also the MMP-14 construct. This exemplary assay can be performed with the inducible MMP-14. In alternative embodiments, the MMP-14 construct is further engineered with a different tag (e.g., MYC or similar, or fused to mCitrine) to enable to test the HA/FLAG ratio on the cell surface in the absence and presence of MMP-14. The ratio between HA and FLAG and not just the FLAG expression level with and without MMP-14 will be a more robust and reliable way to prove cleavage by MMP-14 at the cell surface.

Stable Cell Lines Expressing Each of the Elements Independently—Cleavage as a Result of Cell Cross-Talk:

In alternative embodiments, to further demonstrate that cleavage is indeed at the cell surface, two independent cell lines can be mixed: one expressing the substrate and the second expressing the enzyme. With the right conditions, we should observe a decrease in FLAG signal when these two cell lines are mixed and the enzyme on one encounters the substrate on the other. Even a small decrease in FLAG signal will demonstrate that cleavage occurs at the cell surface and not while travelling to the cell surface through the classical secretory pathway. In addition, a cellular system that relies on two cell lines will have the flexibility of mixing different cell types, one expressing the substrate and the other the enzyme. This can further enhance the flexibility of the cell-based platform for screening.

Assay Utility and Robustness for Monitoring or Assaying Cleavage by MMP-14 and Adaptation to an HTS Platform:

To further increase the robustness of the assay, provided are clones that show the high levels of substrate expression at the cell surface (HA signal), but the lowest FLAG signal in the presence (or induction) of MMP-14. An HTS platform for exemplary assays as provided herein will facilitate the discovery of novel protease inhibitors against MMP-14. The simplicity and potential robustness of assays as provided herein allow for efficient high-throughput screening via flow cytometry and/or fluorescence plate readers or microscopy. In alternative embodiments, to efficiently perform screens, exemplary assays are adapted to a 96- or 384-well format. For that purpose, exemplary assay can use non-adherent stable cell lines such as SupT-1s.

Adaptation to Other Substrate/Protease Pairs:

MMP-14 and its optimized substrate were chosen as the proof-of-principle elements of the cell-based assay due to its well-established robust activity at the cell surface and its importance in cancer and metastasis. The simplicity of the assay design will allow for its straightforward adaptation to other proteases that are catalytically active on the extracellular portion of the plasma membrane. While proven here for MMP-14/MMP-14 substrate pair, the assay is also easily adaptable to any other metalloproteinase or related metalloproteases, including the family of A Disintegrin And Metalloproteases (ADAMs), provided enzyme/substrate pair are available or known. Some other membrane-tethered proteases that contribute to the progression of diseases are exemplified by beta secretase (BACE-1) in Alzheimer's disease, Hemagglutinin (HA) and Neuraminidase (NA) in influenza virus entry and exit respectively, and matriptase in HIV-1 virions spread[25-28]. Adaptation to monitor or assay the proteolytic cleavage activity of BACE-1, for example, seems to be the most feasible and clinically relevant. BACE-1 cleaves Amyloid Precursor Protein (APP) as the precursor step of the aggregation of amyloid plaques that is considered the hallmark of Alzheimer's disease[25,26]. In this adaptation, BACE-1 can be co-expressed with assay constructs harboring an optimized BACE-1 substrate in order to monitor or assay its cleavage activity in the context of the assay.

In the Presence of MMP-14 there is a Drastic Decrease in FLAG Surface Expression:

We have corroborated that in the presence of MMP-14 there is a drastic decrease in FLAG surface expression. When HEK 293T cells were co-transfected with substrate (AHLR) alone, 93% of the cells are FLAG positive. This number decreases to 56% in the presence of a scrambled plasmid, but importantly, drastically decreases to 14% in the presence of MMP-14.

Figure 15A:
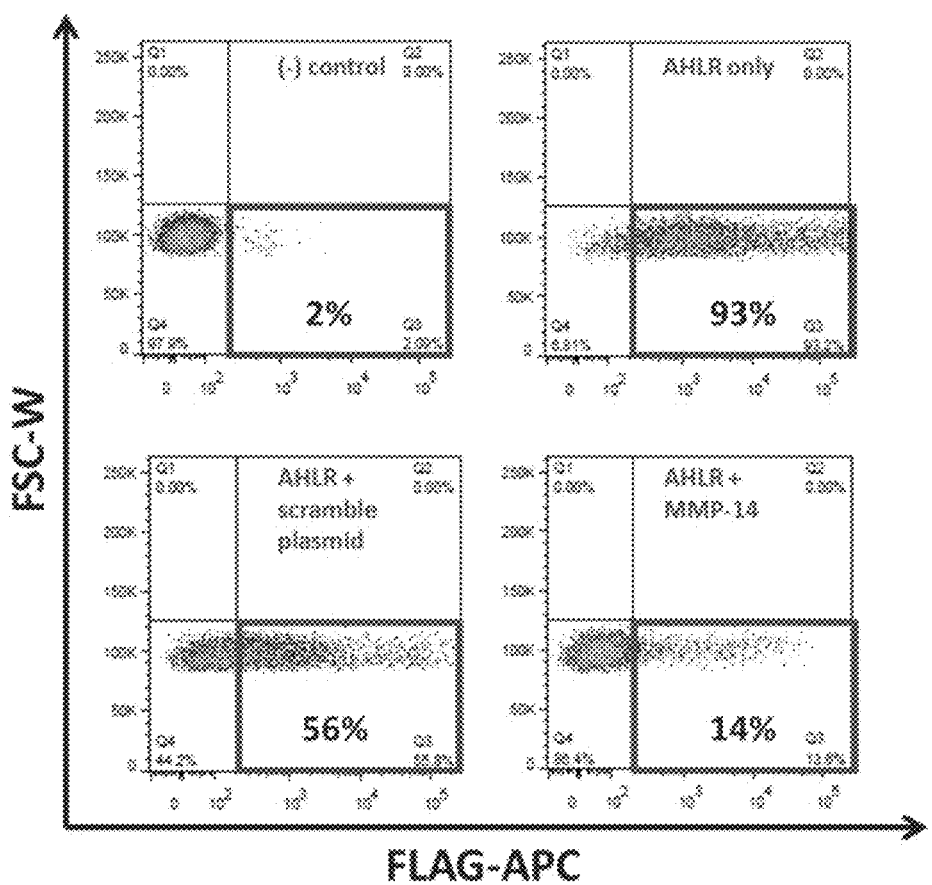
FIG. 15A-B graphically illustrate data from a flow cytometry analysis of cells expressing AHLR and MMP-14 or control plasmid.
Figure 15B:
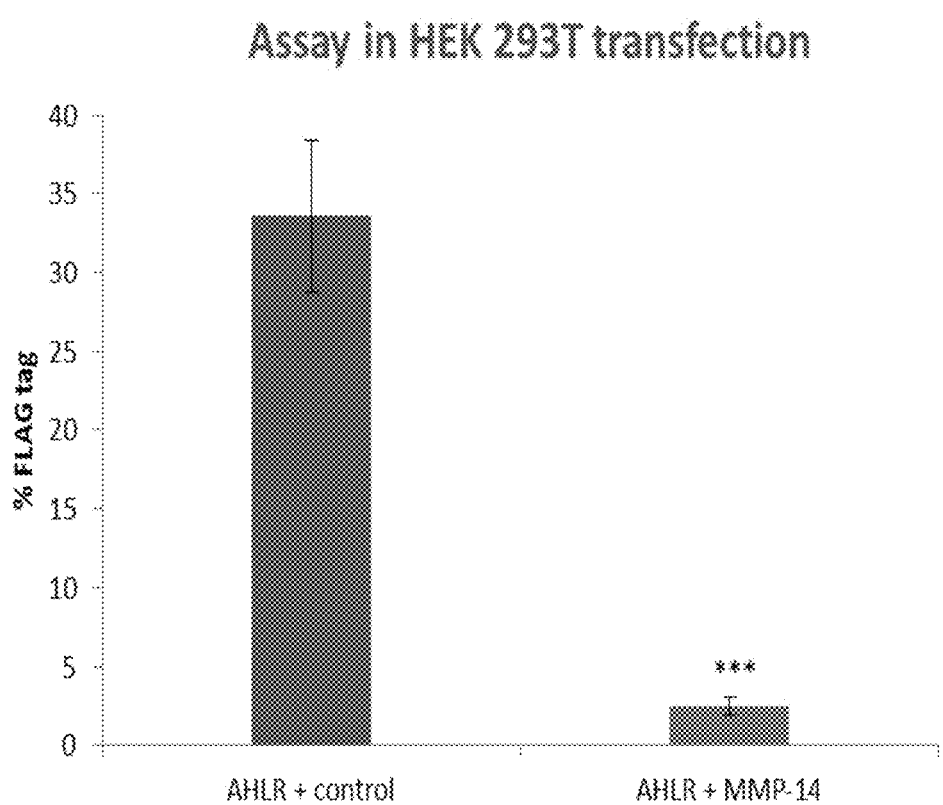
Figure 16A:
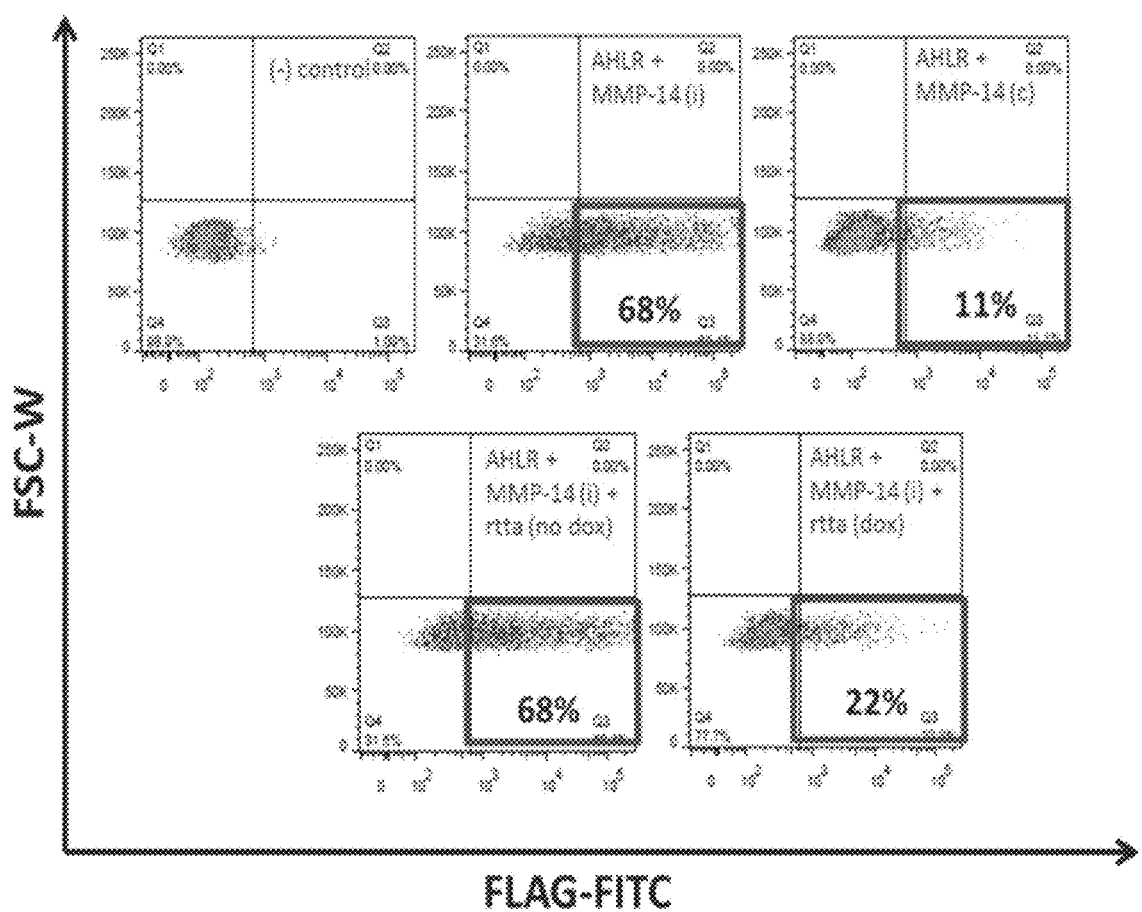
FIG. 16A-D graphically illustrate data from a flow cytometry analysis of MMP-14(i) expression system in HEK 293T cells.
Figure 16B:
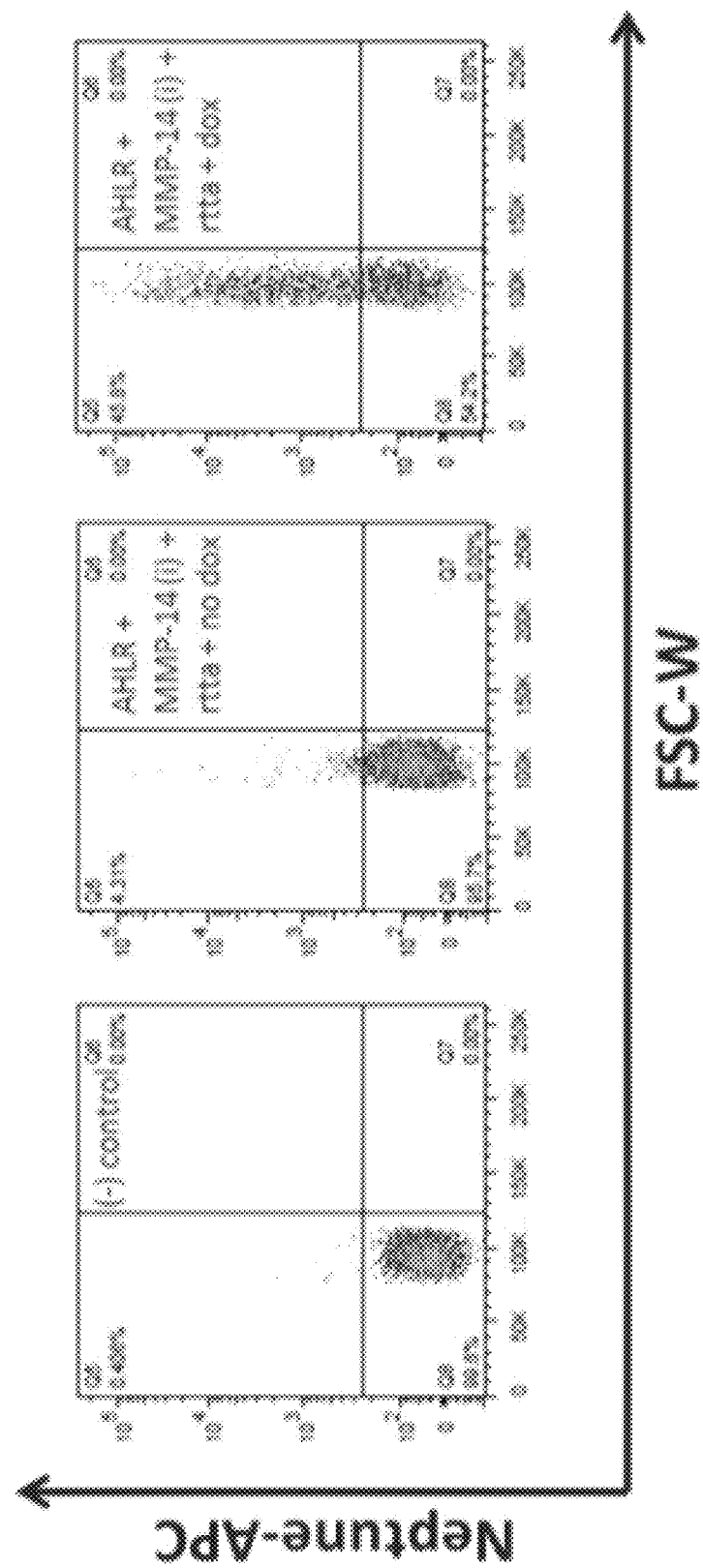
Figure 16C:
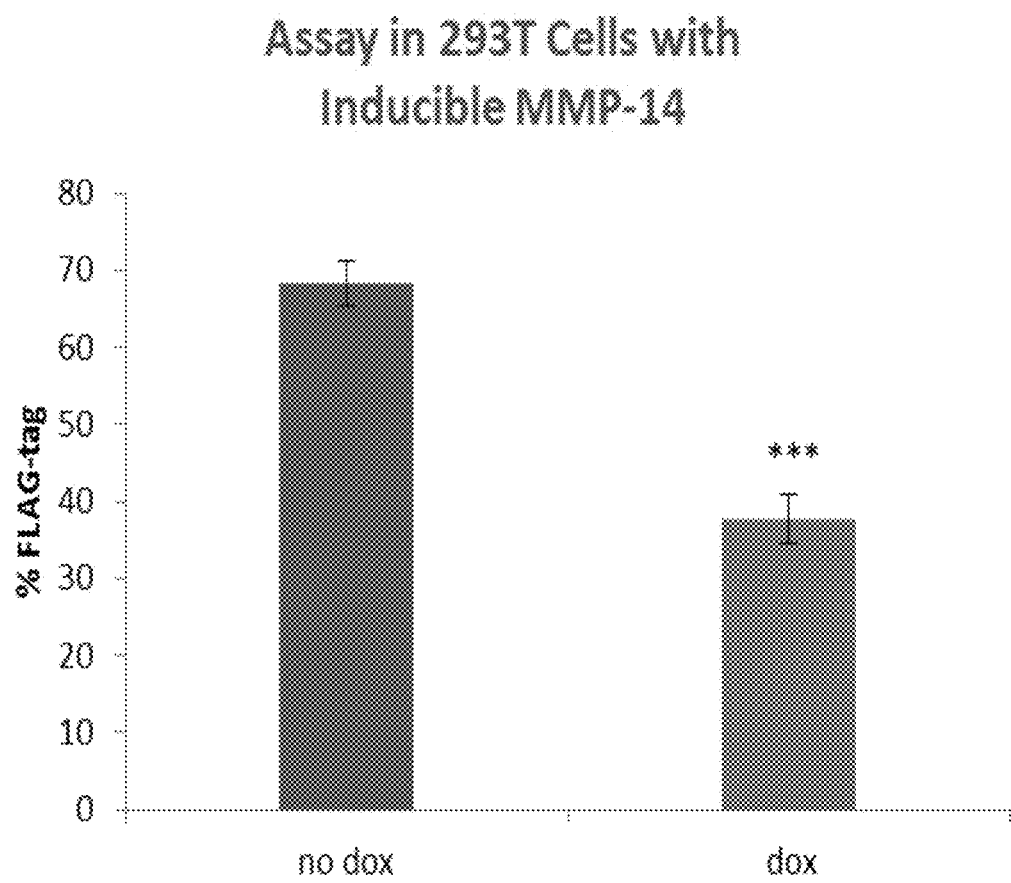
Figure 16D:
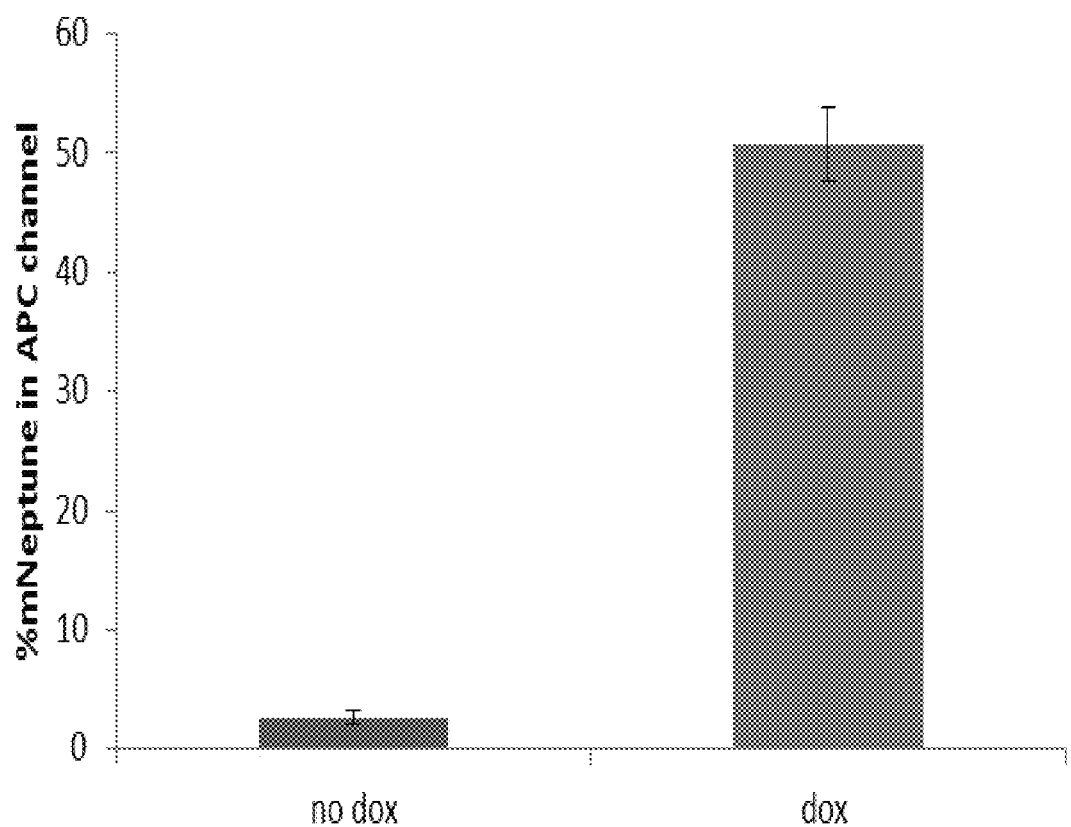

FIG. 15 illustrates data showing a flow cytometry analysis of cells expressing AHLR and MMP-14 or control plasmid. FIG. 15A: FLAG tag expression, as observed in the APC channel, is drastically reduced in the presence of MMP-14 compared to the co-transfection positive control. FIG. 15B: Co-transfection replicate experiments show that the decrease of FLAG tag in the presence of MMP-14 expression is statistically significant with p-value<0.0001 (n=4).

This experiment demonstrates that in the presence of MMP-14 there is a marked reduction in FLAG expression, most likely due to cleavage of the AHLR substrate by the enzyme MMP-14. In order to further demonstrate that the reduction in FLAG signal is due to the presence and activity of the enzyme MMP-14, we have expressed an inducible MMP-14 expression system that should provide stronger evidence for the cleavage of the AHLR substrate by MMP-14. For the sake of simplicity, the Tet-on inducible MMP-14 plasmid would hereafter be referred to as MMP-14(i), whereas the constitutive MMP-14 plasmid would be referred as MMP-14(c). Co-transfection of AHLR substrate, MMP-14(i), and reverse tetracycline-controlled transactivator (rtTA) in HEK-293T cells showed a decrease in FLAG signal from 68% to 22% upon addition of doxycycline (dox). This decrease in FLAG-tag signal was comparable to the constitutive-expression experiment done in parallel in which FLAG tag signal decreased from 68% to 11%. Furthermore, FIG. 5B shows that upon the induction of dox, mNeptune fluorescence protein is significantly higher (mNeptune-APC) signifying both inducibility and expression of MMP-14 protein in the system. mNeptune is linked to the MMP-14 gene through an IRES (internal ribosome entry site) and is used as an additional tracking device for MMP-14 expression.

FIG. 16 illustrates data showing a flow cytometry analysis of MMP-14(i) expression system in HEK 293T cells. FIG. 16A: FLAG tag surface expression in both constitutive and inducible MMP-14 systems. FIG. 16B: Analysis of MMP-14(i), as observed by the expression of the coupled mNeptune fluorescent protein. FIG. 16C: Replicate experiments show the decrease of FLAG surface expression upon MMP-14 induction is statistically significant with p-value<0.0001 (n=4). FIG. 16D: Replicate experiments also show that the mean mNeptune fluorescence protein (indirect marker of MMP-14 expression) increases from 2.6% to 50.7% upon addition of dox.

These experiments, as illustrated in FIG. 15 and FIG. 16, which clearly show a decrease of FLAG surface expression in the presence of MMP-14, were done in transfection experiments.

We then engineered a cell line that stably expresses the AHLR substrate utilizing a retroviral vector carrying the substrate construct. The cell line was referred to as AHLR+. We then transfected AHLR+ cells with the MMP-14 expressing plasmid or a scramble plasmid as negative control. Flow cytometry analysis shows that the overexpression of MMP-14 drastically reduced the FLAG surface expression from 77% to 23%. Replicate experiments further demonstrated the robustness and repeatability in a stable cell line system. MMP-14 expression significantly reduces the mean of the FLAG tag signal in AHLR+ cells from 84.5% to 36.1%.

Figure 17A:
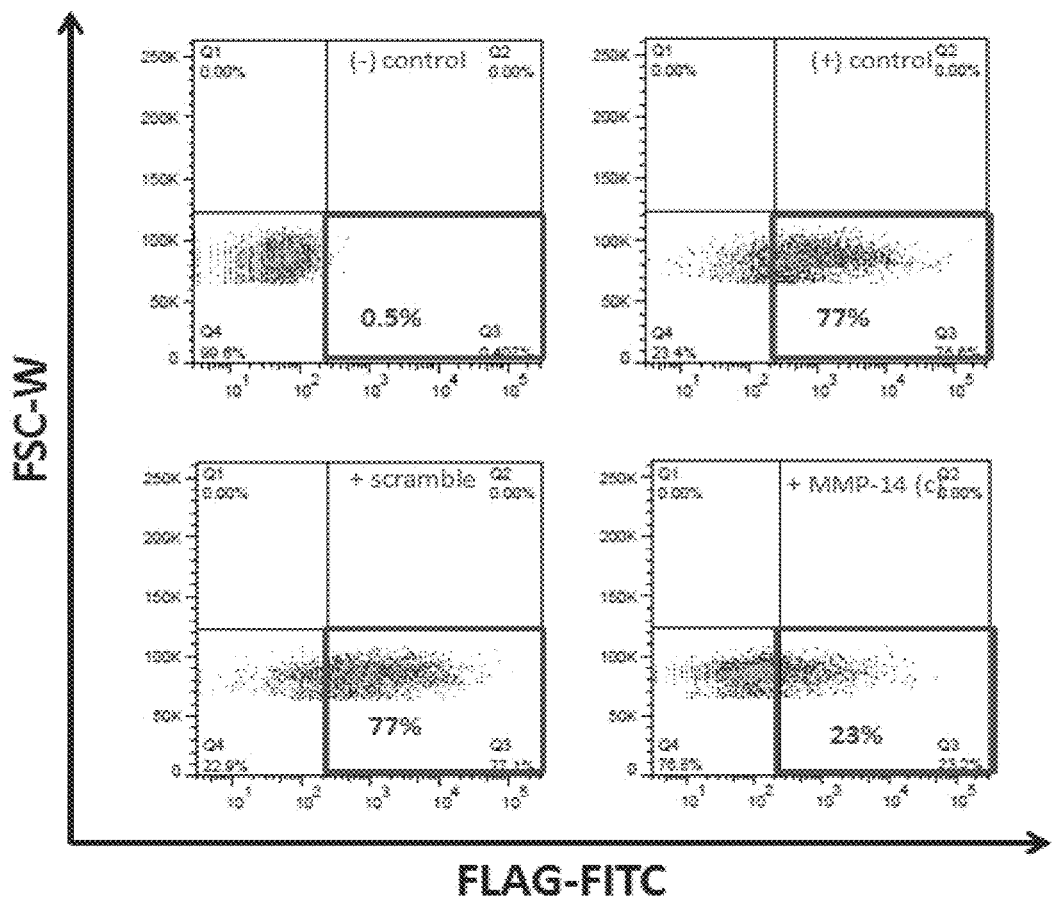
FIG. 17A-B graphically illustrate data from a flow cytometry analysis of constitutive MMP-14 in AHLR+ cells.
Figure 17B:
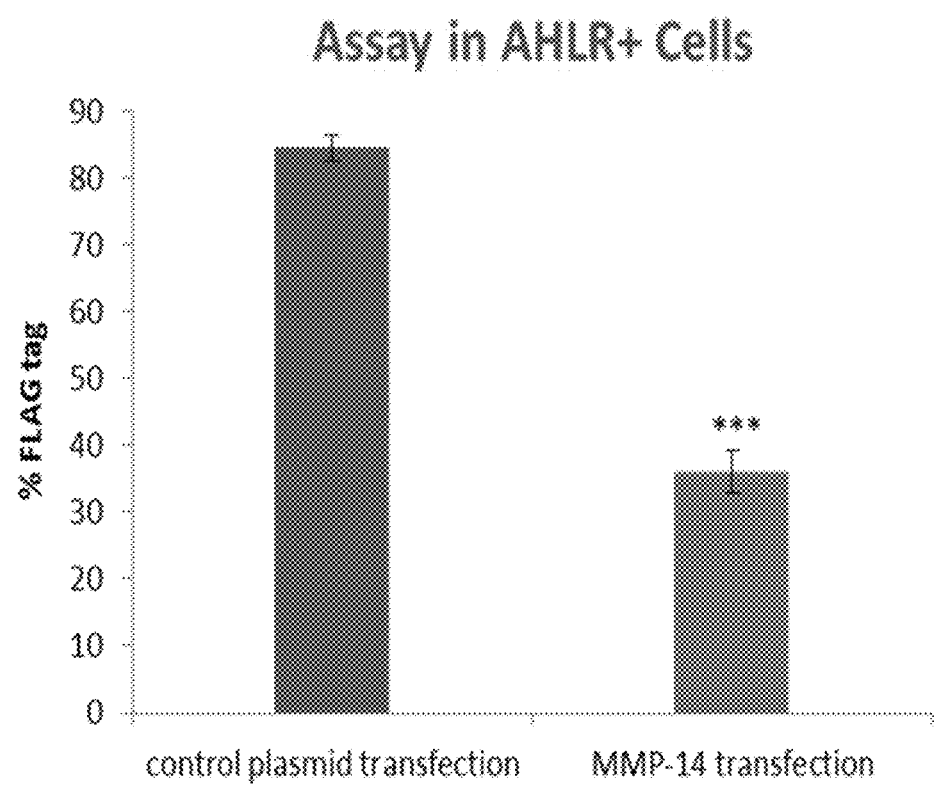

FIG. 17 illustrates data showing flow cytometry analysis of constitutive MMP-14 in AHLR+ cells. FIG. 1A: FLAG signal decreases upon expression of MMP-14. FIG. 17B: Replicate experiments show the decrease of FLAG cell surface expression upon expression of MMP-14 is statistically significant with p-value<0.0001 (n=4). Control plasmid transfection: 84.5±2%; MMP-14 transfection: 36.1±3.3%, We then utilized the same AHLR+ cells but with the inducible MMP-14 system. For that purpose, the AHLR+ cell line was transfected with MMP-14(i) and rtTA plasmid, in the absence or presence of the inducer dox. Flow cytometry analysis shows 87.5% FLAG surface expression prior to MMP-14 induction and 74.8% following addition of dox. While the decrease is not robust, T-test statistical analysis shows that the reduction in mean FLAG signal is statistically significant with a p-value of less than 0.05. This corroborates the previous results in HEK 293T co-transfection system where the MMP-14(c) displays more robust cleavage than with MMP-14(i), at least as analyzed by flow cytometry. In these experiments mNeptune fluorescence protein can be detected in 33.4% of cells upon the addition of dox, showing that the expression of MMP-14 is induced although at lower levels than in the previous experiments.

Figure 18A:
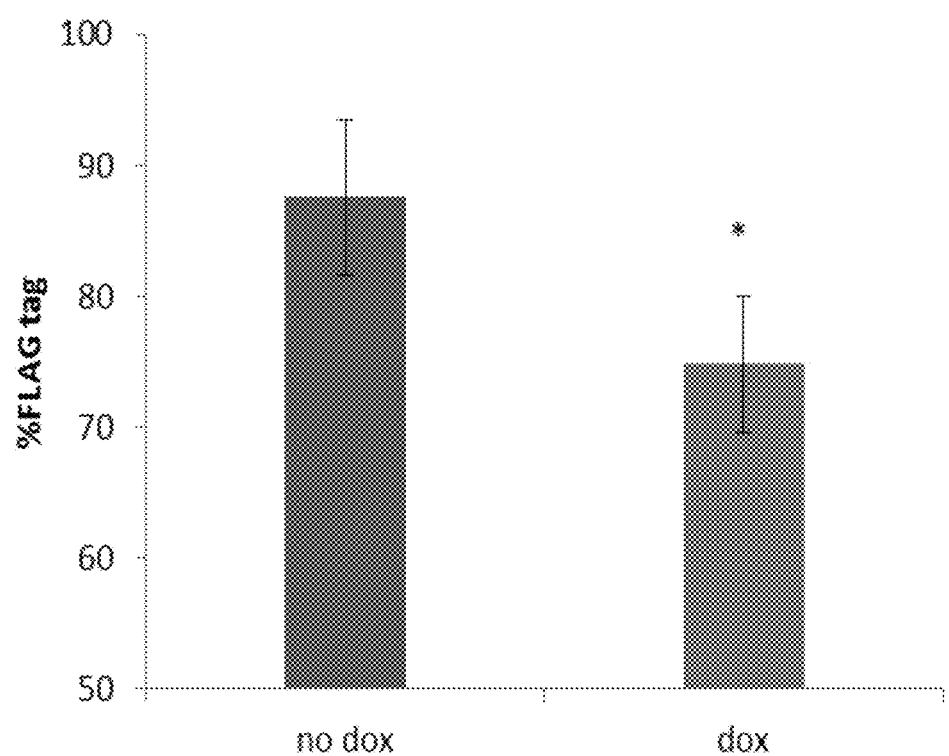
FIG. 18A-B graphically illustrate data from a flow cytometry analysis of MMP-14(i) expression system in AHLR+ cells.
Figure 18B:
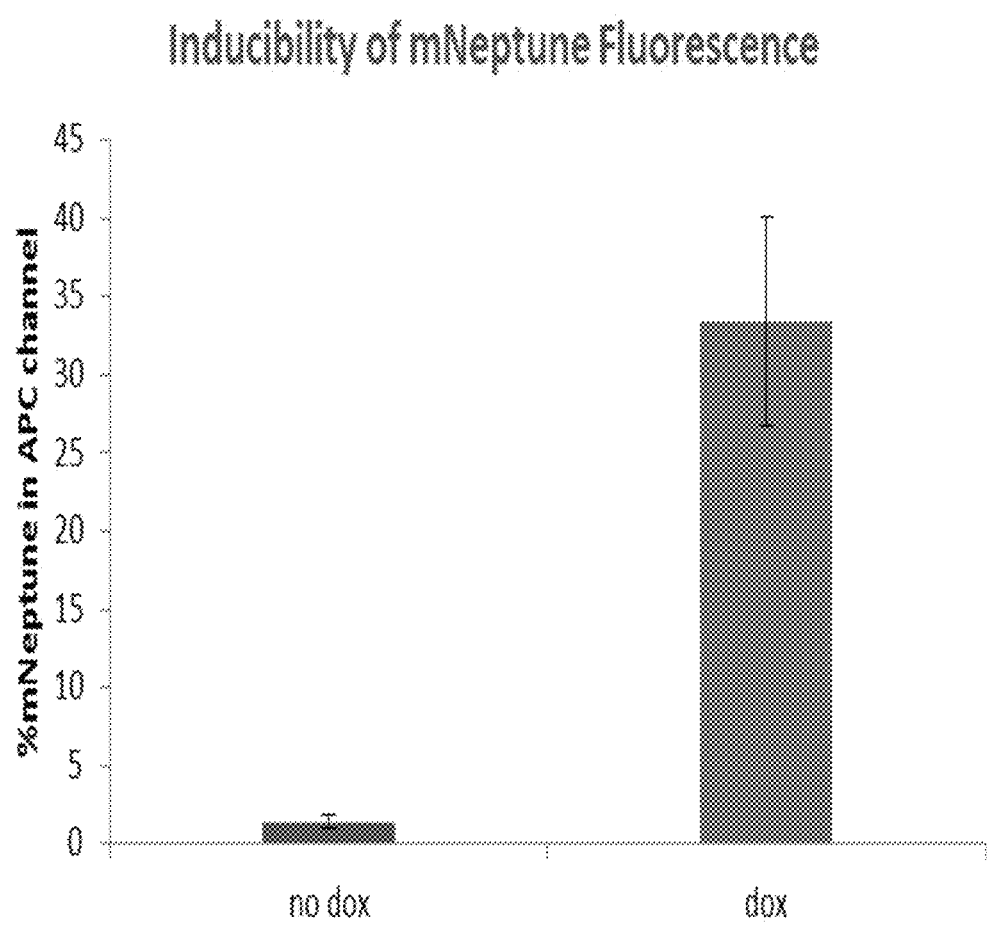

FIG. 18 illustrates data showing flow cytometry analysis of MMP-14(i) expression system in AHLR+ cells. FIG. 18A: Replicate experiments show the decrease of FLAG tag upon the induction of MMP-14 is statistically significant with p-value<0.05 (n=4). A 87.5±5.9% FLAG expression prior to induction of MMP-14 decreases to 74.8±5.2% following MMP-14 induction. FIG. 18B: Replicate experiments also show that the mean mNeptune fluorescence protein dramatically increased from 1.4% with no induction to 33.4% upon dox induction.

A decrease of approximately 14%, while statistically significant, is not as robust as expected, most probably due to the less than perfect expression level of MMP-1, transfection efficiency, leakiness of the system leading to some cleavage prior to induction or all the above. Stable cell lines expressing both the substrate and MMP-14 (constitutive or inducible) should result in a more robust phenotype.

All the results so far clearly pinpoint at cleavage of the AHLR substrate by MMP-14, as demonstrated by the loss of the FLAG tag at the cell surface through classical flow cytometry staining. These results do not prove though that cleavage actually occurred at the cell surface rather than within the classical secretory pathway while both enzyme and substrate travel to the cell surface.

The assay developed here for MMP-14 as proof of principle is intended to specifically monitor or assay cleavage at the cell surface or extracellular matrix, in contrast to the previous assay we have developed that monitors or assays cleavage within the classical secretory pathway (developed for HIV-1 envelope and the premature membrane protein of Dengue virus, both cleaved within the Golgi/transGolgi Network vesicles of the secretory pathway).

Cleavage of the AHLR Substrate Occurs at the Cell Surface:

In order to corroborate that cleavage of the AHLR substrate occurs at the cell surface, we then pursued the development of a cell line stably expressing the enzyme MMP-14, a cell line referred to as MMP-14+. The MMP-14+ cell line, obtained through classical retroviral technology, was then mixed with the substrate-expressing cell line AHLR+. AHLR+ cells and MMP-14+ cells where mixed together at varying ratios. The figure shows a set of experiments where 50,000 (50K) AHLR+ cells were mixed with 175K MMP14+ cells. Parallel experiments where performed with naïve HEK 293T control. Preliminary results showed that at the ratio of $50\times10^3$ AHLR+ cells/17 $5\times10^3$ MMP-14+ cells a substantial decrease of FLAG tag signal is observed. These results clearly demonstrate that cleavage is indeed occurring at the cell surface, and importantly, by MMP-14.

Figure 19:
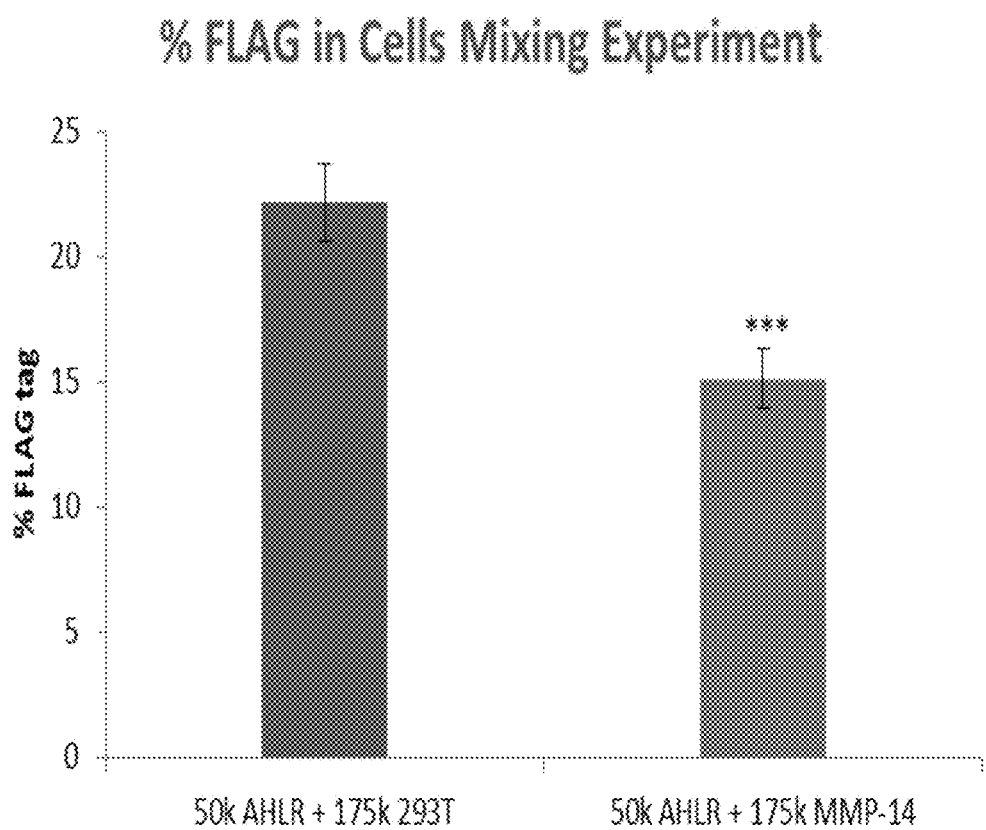
FIG. 19 graphically illustrate data from a flow cytometry analysis of cells following a mixing experiment; replicate experiments show the decrease of FLAG tag upon the incubation with MMP-14+ cells is statistically significant with p-value<0.0001 (n=5), as described in detail in Example 1, below.
Figure 20:
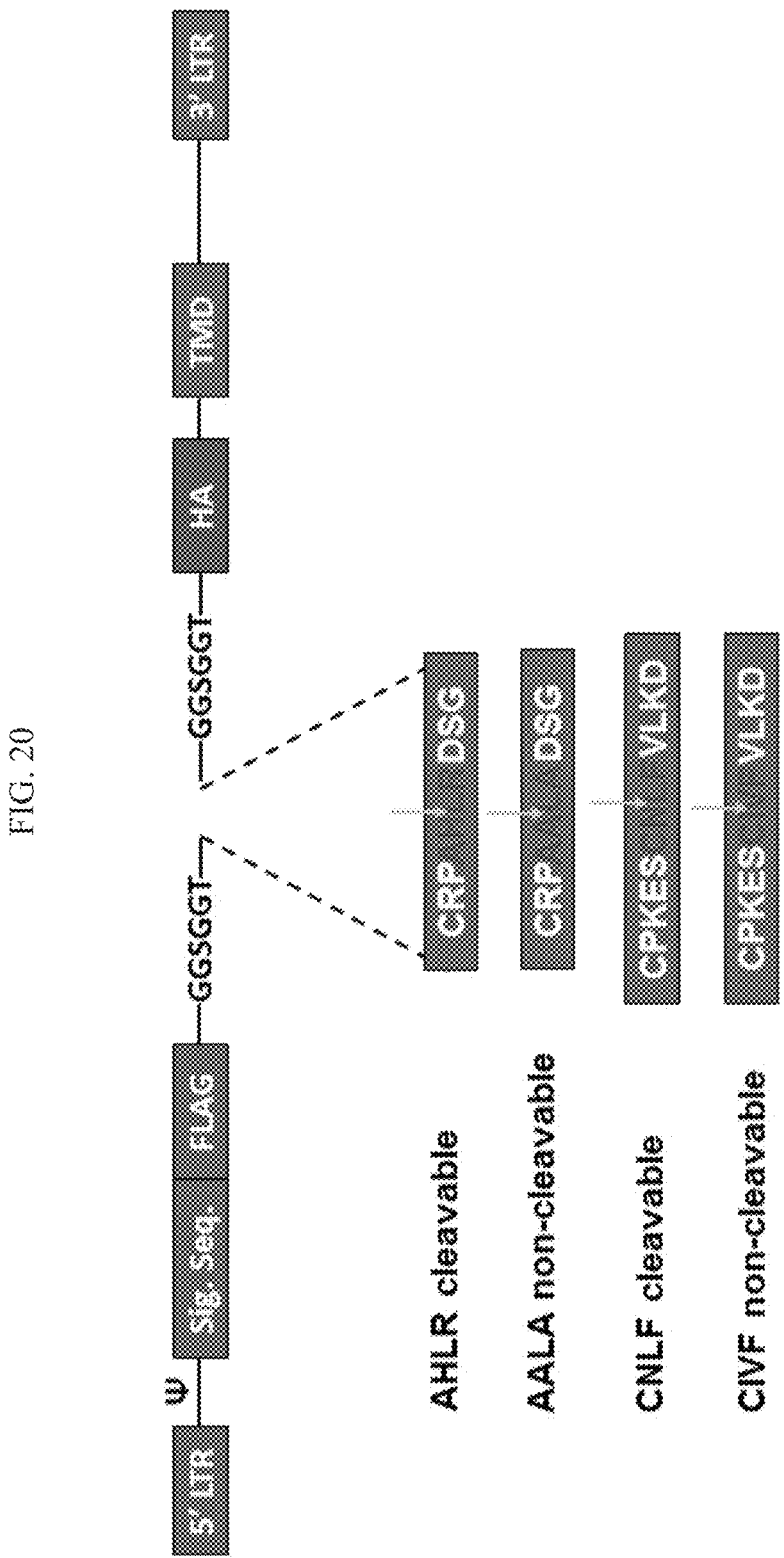
FIG. 20 schematically illustrates exemplary assay constructs in a retroviral plasmid, where (SEQ ID NO:1) CRPAHLRDSG, and (SEQ ID NO:3) AHLR is cleavable; (SEQ ID NO:9) CRPAALADSG, and (SEQ ID NO:14) AALA is non-cleavable; (SEQ ID NO:10) CPKESCNLFVLKD, and (SEQ ID NO:15) CNLF is cleavable; (SEQ ID NO:11) CPKESCIVFVLKD, and (SEQ ID NO:16) CIVF is non-cleavable; as described in detail in Example 1, below.

FIG. 19 illustrates data from a flow cytometry analysis of cells following a mixing experiment. Replicate experiments show the decrease of FLAG tag upon the incubation with MMP-14+ cells is statistically significant with p-value<0.0001 (n=5). Control mixing experiment: 22.2±1.5%; Experimental mixing experiment: 15.2±1.2%.

Additional exemplary cell lines with additional controls are:
- a mutant version of the AHLR (SEQ ID NO:3) cleavage site, AALA SEQ ID NO:14), as negative control;
- an additional substrate, CNLF (SEQ ID NO:15), to show that the assay can be used broadly for monitoring or assaying cleavage at the cell surface and is not specific to AHLR (SEQ ID NO:3);
- a mutant version of the CNLF (SEQ ID NO:15) cleavage site, CIVF SEQ ID NO:16), as an additional negative control;
- where both the CNLF (SEQ ID NO:15) and AHLR (SEQ ID NO:3) cleavable sites are based on both: Ouyang M, Huang H, Shaner N C, et al. Simultaneous visualization of protumorigenic Src and MT1-MMP activities with fluorescence resonance energy transfer. Cancer Res. 2010; 70(6): 2204-2212; and, Lu S, Wang Y, Huang H, et al. Quantitative FRET imaging to visualize the invasiveness of live breast cancer cells. PLoS ONE. 2013; 8(3):e58569.

CONCLUSIONS

Compositions and assays as provided herein are adaptable to other protease-substrates, and they are adaptable in tandem.

While the MMP-14/CRPAHLRDSG (SEQ ID NO:1) protease-substrate tandem was chosen as a proof-of-principle for the assay, the assay is adaptable to any substrate cleaved by any of the enzymes that work in the classical secretory pathway or in the extracellular matrix (ECM) or at the cell surface, or is adaptable to other protease-substrate couples as long as both substrate and protease are co-localized at the cell surface, and the protease is active at the cell surface, or on the outer surface of a membrane, a liposome or an exosome, or extracellular matrix.

This is true whether the enzyme and or substrate are linked/attached/embedded to/within the cell membrane or secreted into the extracellular matrix, such as many metalloproteinases.

The mixing experiment of cells carrying a substrate and other distinct cells carrying the enzyme prove without any doubt that the assay can monitor or assay cleavage at the cell surface.

Different ratios of substrate/enzyme-expressing cells can be used to optimize cleavage at the cell surface.

Exemplary compositions and assays provided herein can also be utilized to corroborate and monitor or assay for cleavage at the cell surface of a substrate embedded within the cell surface and cleaved by a secreted enzyme or an enzyme in the extracellular matrix or supernatant.

Exemplary compositions and assays provided herein are adaptable to drug discovery:

For drug discovery, compositions and assays provided herein are easy to use, reproducible, robust, and able to be miniaturized for a high-throughput (HTS) application.

compositions and assays provided herein are expressed in cells in a biologically significant background and thus it is biologically relevant, in contrast to biochemical assays; compositions and assays provided herein are easy to use and can be easily used, or analyzed, as a cell-based platform by flow cytometry or plate reader/microscopy set-ups.

compositions and assays provided herein are versatile, and they allow for the screening for inhibitors against other cell membrane proteases, and it is thus not restricted to MMP-14 inhibitors.

REFERENCES

1. Neurath H, Walsh K A. Role of proteolytic enzymes in biological regulation (a review). Proc Natl Acad Sci USA. 1976; 73(11):3825-32.
2. Saido T, Leissring M A. Proteolytic degradation of amyloid β-protein. Cold Spring Harb Perspect Med. 2012; 2(6):a006379.
3. Shpacovitch V, Feld M, Hollenberg M D, Luger T A, Steinhoff M. Role of protease-activated receptors in inflammatory responses, innate and adaptive immunity. J Leukoc Biol. 2008; 83(6):1309-22.
4. Stolp Z D, Stotland A, Diaz S, Hilton B J, Burford W, Wolkowicz R. A Novel Two-Tag System for Monitoring Transport and Cleavage through the Classical Secretory Pathway—Adaptation to HIV Envelope Processing. PLoS ONE. 2013; 8(6):e68835.
5. Dalbey R E, Von Heijne G (1992) Signal peptidases in prokaryotes and eukaryotes—a new protease family. Trends Biochem Sci 17: 474-478.
6. Seidah N G, Prat A (2012) The biology and therapeutic targeting of the proprotein convertases. Nat Rev Drug Discov 11: 367-383.
7. Burrage P S, Mix K S, Brinckerhoff C E. Matrix metalloproteinases: role in arthritis. Front Biosci. 2006; 11:529-43.
8. Itoh Y, Palmisano R, Anilkumar N, Nagase H, Miyawaki A, Seiki M. Dimerization of MT1-MMP during cellular invasion detected by fluorescence resonance energy transfer. Biochem J. 2011; 440(3):319-26.
9. Nagase H, Visse R, Murphy G. Structure and function of matrix metalloproteinases and TIMPs. Cardiovasc Res. 2006; 69(3):562-73.
10. Pietraszek K, Chatron-colliet A, Brézillon S, et al. Lumican: A new inhibitor of matrix metalloproteinase-14 activity. FEB S Lett. 2014; 588(23):4319-24.
11. Jiang A, Lehti K, Wang X, Weiss S J, Keski-oja J, Pei D. Regulation of membrane-type matrix metalloproteinase 1 activity by dynamin-mediated endocytosis. Proc Natl Acad Sci USA. 2001; 98(24):13693-8.
12. Zarrabi K, Dufour A, Li J, et al. Inhibition of matrix metalloproteinase 14 (MMP-14)-mediated cancer cell migration. J Biol Chem. 2011; 286(38):33167-77.
13. Sounni N E, Paye A, Host L, Noel A. MT-MMPS as Regulators of Vessel Stability Associated with Angiogenesis. Front Pharmacol. 2011; 2:111.
14. Haage A, Nam D H, Ge X, Schneider I C. Matrix metalloproteinase-14 is a mechanically regulated activator of secreted MMPs and invasion. Biochem Biophys Res Commun. 2014; 450(1):213-8.
15. Sabeh F, Ota I, Holmbeck K, et al. Tumor cell traffic through the extracellular matrix is controlled by the membrane-anchored collagenase MT1-MMP. J Cell Biol. 2004; 167(4):769-81.
16. Sendon-lago J, Seoane S, Eiro N, et al. Cancer progression by breast tumors with Pit-1-overexpression is blocked by inhibition of Metalloproteinase (MMP)-13. Breast Cancer Res. 2014; 16(6):505
17. Williams K C, Coppolino M G. Phosphorylation of membrane type 1-matrix metalloproteinase (MT1-MMP) and its vesicle-associated membrane protein 7 (VAMP7)-dependent trafficking facilitate cell invasion and migration. J Biol Chem. 2011; 286(50):43405-16.
18. Ouyang M, Lu S, Li X Y, et al. Visualization of polarized membrane type 1 matrix metalloproteinase activity in live cells by fluorescence resonance energy transfer imaging. J Biol Chem. 2008; 283(25):17740-8.
19. Ouyang M, Huang H, Shaner N C, et al. Simultaneous visualization of protumorigenic Src and MT1-MMP activities with fluorescence resonance energy transfer. Cancer Res. 2010; 70(6):2204-12.
20. Lu S, Wang Y, Huang H, et al. Quantitative FRET imaging to visualize the invasiveness of live breast cancer cells. PLoS ONE. 2013; 8(3):e58569.
21. Coppola J M, Bhojani M S, Ross B D, Rehemtulla A. A small-molecule furin inhibitor inhibits cancer cell motility and invasiveness. Neoplasia. 2008; 10(4):363-70.
22. Bassi D E, Lopez de cicco R, Mahloogi H, Zucker S, Thomas G, Klein-szanto AJ. Furin inhibition results in absent or decreased invasiveness and tumorigenicity of human cancer cells. Proc Natl Acad Sci USA. 2001; 98(18):10326-31.
23. Ma Y C, Fan W J, Rao S M, Gao L, Bei Z Y, Xu S T. Effect of Furin inhibitor on lung adenocarcinoma cell growth and metastasis. Cancer Cell Int. 2014; 14:43.
24. Becker G L, Sielaff F, Than M E, et al. Potent inhibitors of furin and furin-like proprotein convertases containing decarboxylated P1 arginine mimetics. J Med Chem. 2010; 53(3):1067-75.
25. O'brien R J, Wong P C. Amyloid precursor protein processing and Alzheimer's disease. Annu Rev Neurosci. 2011; 34:185-204.
26. Murphy M P, Levine H. Alzheimer's disease and the amyloid-beta peptide. J Alzheimers Dis. 2010; 19(1):311-23.
27. Wood M P, Cole A L, Eade C R, Chen L M, Chai K X, Cole A M. The HIV-1 gp41 ectodomain is cleaved by matriptase to produce a chemotactic peptide that acts through FPR2. Immunology. 2014; 142(3):474-83.
28. Steinhauer D A. Role of hemagglutinin cleavage for the pathogenicity of influenza virus. Virology. 1999; 258(1):1-20.
29. Van duijnhoven SM, Robillard M S, Nicolay K, Grull H. Development of Radiolabeled Membrane Type-1 Matrix Metalloproteinase Activatable Cell Penetrating Peptide Imaging Probes. Molecules. 2015; 20(7):12076-92.

30. Egawa N, Koshikawa N, Tomari T, Nabeshima K, Isobe T, Seiki M. Membrane type 1 matrix metalloproteinase (MT1-MMP/MMP-14) cleaves and releases a 22-kDa extracellular matrix metalloproteinase inducer (EMMPRIN) fragment from tumor cells. J Biol Chem. 2006; 281(49):37576-85.
31. Zhu L, Zhang F, Ma Y, et al. In vivo optical imaging of membrane-type matrix metalloproteinase (MT-MMP) activity. Mol Pharm. 2011; 8(6):2331-8.
32. Okumura Y, Sato H, Seiki M, Kido H. Proteolytic activation of the precursor of membrane type 1 matrix metalloproteinase by human plasmin. A possible cell surface activator. FEBS Lett. 1997; 402(2-3):181-4.
33. Sato T, Kondo T, Fujisawa T, Seiki M, Ito A. Furin-independent pathway of membrane type 1-matrix metalloproteinase activation in rabbit dermal fibroblasts. J Biol Chem. 1999; 274(52):37280-4.
34. Itoh Y. Membrane-type matrix metalloproteinases: Their functions and regulations. Matrix Biol. 2015; 44-46:207-23.
35. Brinckerhoff C E, Matrisian L M. Matrix metalloproteinases: a tail of a frog that became a prince. Nat Rev Mol Cell Biol. 2002; 3(3):207-14.
36. Solanas G, Cortina C, Sevillano M, Batlle E. Cleavage of E-cadherin by ADAM10 mediates epithelial cell sorting downstream of EphB signalling. Nat Cell Biol. 2011; 13(9):1100-7.
37. Kemmler W, James D. Peterson, Donald F. Steiner. Studies on the conversion of proinsulin to insulin. 1. Conversion in vitro with trypsin and carboxypeptidase B. J Biol Chem. 1971; 246(22):6780-6791.

A number of embodiments of the invention have been described. Nevertheless, it will be understood that various modifications may be made without departing from the spirit and scope of the invention. Accordingly, other embodiments are within the scope of the following claims.

What is claimed is:

1. A cell-based method for monitoring or assaying the activity of a protease enzyme of interest, comprising:
   (1) (a) providing a nucleic acid encoding a scaffold protein operatively linked to a transcriptional regulatory unit, wherein the scaffold protein comprises:
   (i) a signal sequence (SS) or any amino acid motif that places the scaffold protein on the extracellular surface of the cell, or on the outer surface of a membrane, a liposome or an exosome;
   (ii) a first tag capable of being specifically recognized by or bound to by a first detectable moiety;

(iii) an amino acid motif or subsequence susceptible to cleavage by the protease enzyme under physiologic or cell culture conditions;

(iv) a second tag capable of being specifically recognized by or bound to by a second detectable moiety; and (v) a transmembrane domain or moiety attaching the scaffold protein to the extracellular surface, or on the outer surface of a membrane, a liposome or an exosome, or keeping the scaffold protein onto the extracellular surface, or on the outer surface of a membrane, a liposome or an exosome;

(b) providing a nucleic acid encoding the protease enzyme of interest in a construct that places the protease enzyme of interest on the cell surface or expresses the protease enzyme of interest extracellularly, or providing the protease enzyme of interest to the extracellular surface of the cell, or on the outer surface of a membrane, a liposome or an exosome;

(c) inserting or transfecting the nucleic acid of (a), and optionally also the nucleic acid (b) if the cell does not already endogenously express the protease enzyme of interest;

(d) expressing or co-expressing the nucleic acid of (a), and if (b) is also inserted, also expressing the nucleic acid of (b), in the cell, or expressing only the nucleic acid of (a) in the cell if the cell already expresses the protease enzyme of interest endogenously; and (e) determining whether the scaffold protein is expressed and attached or otherwise held onto the extracellular surface of the cell, or on the outer surface of a membrane, a liposome or an exosome.

2. The cell-based method of claim 1, wherein the protease enzyme is a zinc-dependent proteolytic enzyme.

3. The cell-based method of claim 1, wherein the protease enzyme is a human protease enzyme, or the protease enzyme expressed in the cell is an engineered or a synthetic enzyme.

4. The cell-based method of claim 2, wherein the protease is or comprises:

(a) a zinc-dependent proteolytic enzyme;
(b) a Matrix Metalloproteinase (MMP);
(c) an ADAM (a disintegrin and metalloproteinase) protease,
wherein optionally the ADAM protease comprises or is an ADAM-10 protease;
(c) a viral protease;
(d) a protease within the classical secretory pathway at the cell surface;
(e) an extracellular matrix protease (ECM).

5. The cell-based method of claim 4, wherein the viral protease is or comprises a Neuraminidase (NA), an HIV-1 protease, a Hepacivirus protease, a Flaviviridae protease, G47, or a Filoviridae virus protease, and optionally the Hepacivirus virus protease is a Hepatitis C Virus (HCV) protease,
and optionally the Flaviviridae virus protease is a Zika virus or a Dengue Virus (DenV) protease,
and optionally the Filoviridae is an Ebolavirus.

6. The cell-based method of claim 1, further comprising screening for an inhibitor or competitor of the enzyme by:

(a) providing a compound to be screened as an inhibitor or competitor of the enzyme;
(b) contacting a plurality of the cells expressing the scaffold protein on their extracellular surfaces, or on the outer surface of a membrane, a liposome or an exosome, or extracellular matrices (ECM) with the compound, and optionally culturing the cells for a period of time, wherein optionally the period of time is between about one minute to one hour; and (c) determining whether the second or membrane-distal tag of the scaffold protein remains expressed on the extracellular surface, or on the outer surface of a membrane, a liposome or an exosome, or ECM of the cell, wherein detecting the presence of the second or membrane-distal tag of the scaffold protein on the cell or in the ECM indicates that the enzyme is significantly inhibited by the compound, and not detecting the presence of the second or membrane-distal tag of the scaffold protein on the cell or in the ECM indicates that the enzyme is not significantly inhibited by the compound.

7. The cell-based method of claim 1, further comprising running a negative control comprising dividing the plurality of the cells co-expressing the scaffold-expressing nucleic acid and not adding the compound to be screened as an inhibitor to one of the divided cell samples.

8. The cell-based method of claim 1, further comprising running a positive control comprising dividing the plurality of the cells co-expressing the scaffold-expressing nucleic acid and adding a known inhibitor or competitor of the enzyme to one of the divided cell samples.

9. The cell-based method of claim 1, wherein the scaffold-expressing nucleic acid comprises a transcriptional regulatory unit comprising a promoter, optionally an inducible promoter or a constitutive promoter.

10. The cell-based method of claim 1, wherein the cell is a mammalian cell, a monkey cell or a human cell, or a lymphocyte or a hepatocyte, or a T cell, and optionally the cells are genetically bar-coded.

11. The cell-based method of claim 1, wherein a detectable moiety is detected or measured on the extracellular surface of the cell, or on the outer surface of a membrane, a liposome or an exosome, by a high throughput screen, a plate-reader, a flow cytometry or microscope visualization.

12. The cell-based method of claim 6, wherein the compound to be screened as an inhibitor or competitor of the enzyme comprises a small molecule, a nucleic acid, a polypeptide or peptide, a peptidomimetic, a polysaccharide or a lipid, or is a member of a library of compounds to be screened, or is a member of a random peptide library or a chemical compound library.

13. The cell-based method of claim 1, wherein two or more, or a plurality of enzymes are screened in the same cell, or on separate cells, wherein optionally the separate cells are mixed in the assay,
and optionally the plurality of enzymes they are variants of the same enzyme, or different enzymes, or a combination thereof.

14. The cell-based method of claim 1, wherein the nucleic acid encoding the scaffold protein further comprises a sequence encoding a flexible peptide linker, and optionally the flexible peptide linker comprises a glycine-comprising linker,
optionally the glycine-comprising linker is a four-, 5- or 6-glycine linker, optionally 1 to six repeats of a glycine linker GGGGS (SEQ ID NO:4).

15. The cell-based method of claim 1, wherein a flexible linker is positioned between the transmembrane domain or moiety attaching the scaffold protein to the extracellular surface and a membrane-proximal tag, and optionally the membrane-proximal tag comprises a FLAG tag (DYKDDDDK) (SEQ ID NO:12) or an HA tag (YPYDVPDYA) (SEQ ID NO:13).

16. The cell-based method of claim 1, further comprising a fluorescent protein positioned in the scaffold protein amino terminal to the tag distal to the cell surface, and optionally the fluorescent protein comprises an mCitrine fluorescence protein.

17. The cell-based method of claim 1, wherein the first tag is an epitope tag capable of being specifically recognized by or bound to by a first antibody or epitope binding unit, and optionally the first antibody is detectable and optionally the antibody or epitope binding unit is a fluorescently tagged.

18. The cell-based method of claim 1, wherein the second tag comprises an epitope tag capable of being specifically recognized by or bound to by a second antibody or epitope binding unit, and optionally the second antibody is detectable, and optionally the antibody or epitope binding unit is a fluorescently tagged antibody.

19. The cell-based method of claim 1, wherein the first detectable moiety that binds or recognizes the first epitope tag does not bind to or recognize the second epitope tag, and the second detectable moiety that binds or recognizes the second epitope tag does not bind to or recognize the first epitope tag, and optionally the first detectable moiety is or comprises an antibody or an epitope binding unit, and optionally the second detectable moiety is or comprises an antibody or an epitope binding unit.

20. The cell-based method of claim 1, wherein the enzyme of interest assayed is endogenous to the cell and is expressed on the cell surface, or on the outer surface of a membrane, a liposome or an exosome.

21. The cell-based method of claim 4, wherein the MMP is: a MMP-14 protease, a membrane-type MMP (MT-MMP) protease, a MT1-protease, a MT2-protease, a MT3-protease, a MT4-protease, a MT5-protease or a MT6-MMP protease.

* * * * *